United States Patent [19]
Haseloff et al.

[11] Patent Number: 5,863,774
[45] Date of Patent: Jan. 26, 1999

[54] CELL ABLATION USING TRANS-SPLICING RIBOZYMES

[75] Inventors: James Haseloff, Cambridge, Mass.;
Andrea Brand, Comberton, England;
Norbert Perrimon, Brookline; Howard M. Goodman, Newton, both of Mass.

[73] Assignees: The General Hospital Corporation, Boston; President and Fellows of Harvard College, Cambridge, both of Mass.

[21] Appl. No.: 486,569

[22] Filed: Jun. 7, 1995

Related U.S. Application Data

[60] Division of Ser. No. 90,193, Dec. 23, 1993, Pat. No. 5,641,673, which is a continuation-in-part of Ser. No. 642,330, Jan. 17, 1991, abandoned.

[51] Int. Cl.$^6$ ............................ C12N 15/00; C12N 15/85; C12Q 1/68
[52] U.S. Cl. ..................... 435/172.3; 435/6; 435/91.31; 435/325; 536/23.2; 536/24.5
[58] Field of Search .............................. 435/172.3, 69.1, 435/91.1, 91.3, 91.4, 320.1; 935/3–6, 9, 10, 20, 21, 23, 24, 34, 35, 43, 44, 52, 55; 800/2, 205; 536/23.2, 23.5, 24.1, 24.5, 25.1

[56] References Cited

U.S. PATENT DOCUMENTS

| | | | |
|---|---|---|---|
| 5,037,746 | 8/1991 | Cech et al. | 435/91 |
| 5,409,823 | 4/1995 | Crossland et al. | 435/172.3 |

FOREIGN PATENT DOCUMENTS

| | | |
|---|---|---|
| 0 240 208 | 10/1987 | European Pat. Off. . |
| 0 321 201 | 6/1989 | European Pat. Off. . |
| WO 87/03451 | 6/1987 | WIPO . |
| WO 88/04300 | 6/1988 | WIPO . |
| WO 89/05852 | 6/1989 | WIPO . |
| WO 90/11364 | 10/1990 | WIPO . |
| WO 90/13654 | 11/1990 | WIPO . |
| WO 91/06302 | 5/1991 | WIPO . |
| WO 91/14699 | 10/1991 | WIPO . |
| WO 92/13090 | 8/1992 | WIPO . |

OTHER PUBLICATIONS

Yagi, T. et al., "Homologous Recombination at c–fyn Locus of mouse embryonic stem cells with use of diphtheria toxin A–fragment gene in negative slection," *Proc. Natl. Acad. Sci. USA* 87:9918–9922. (Dec. 1990).
Zaug, A.J. et al., "Intervening Sequence RNA of Tetrahymena is an Enzyme," *Science* 231:470–475 (1986).
Agabian, N., "Trans Splicing of Nuclear Pre–mRNAS," *Cell* 61 (7):1157–1160 (Jun. 1990).
Barinaga, M., "Ribozymes: Killing the Messenger," *Science* 262:1512–1514 (1993).
Been, M.D. et al., "One binding site determines sequence specificity of Tetrahymena pre–mRNA self splicing, trans–splicing, and RNA enzyme activity," *Cell* 47(2):207–216 (1986).

Been, M.D. et al., "Selection of Circularization Sites in a Group 1 IVS RNA Requires Multiple Alignments of an Internal Template–Like Sequence," *Cell* 50:951–961 (1987).
Brand, A. et al., "A General Method for Directed Gene Expression in Drosophila," Presented at The Genome Conference, 13th Annual Conference on the Organisation and Expression of the Genome, Victoria, Australia, Feb. 18–22, 1991, SYM–15–2.
Brand, A.H. et al., "Targeted Gene Expression in Drosophila melanogaster," *J. Cell Biochem. Supp. 14E* (Mar.–Apr. 1990), Abstracts, 19th Annual UCLA Symposia, Abst. P201, p. 153.
Breitman, M.L. et al., "Genetic Ablation: Targeted Expression of a Toxin Gene Causes Microphthalmia in Transgenic Mice," *Science* 238:1563–1565 (1987).
Cech, T.R., "Self–Splicing of Group I Introns," *Ann. Rev. Biochem.* 59: 543–568 (Jul. 1990).
Cech, T.R., "Conserved sequences and structures of group I introns: building an active site for RNA catalysis—a review," *Gene* 73:259–271 (1988).
Chaut, J.C. et al., "Can Ribozymes Be Used to Regulate Procaryote Gene Expression?," *Biochem. Biophys. Res. Commun.* 162(3):1025–1029 (1989).
Cotten, M. et al., "Ribozyme Mediated Destruction of RNA in vivo," *EMBO J.* 8(12):3861–3866 (1989).
Cotten, M., "The in vivo application of ribozymes," *Trends Biotech.* 8(7):174–178 (Jul. 1990).
Doudna, J.A. et al., "RNA structure, not sequences, determines the 5' splice–site specificity of a group I intron," *Proc. Natl. Acad. Sci.* 86:7402–7406 (1989).
Evans, G.A., "Dissecting mouse development with toxigenics," *Genes and Develop.* 3:259–263 (1982).
Fischer, J.A. et al., "GAL4 activates transcription in Drosophila," *Nature* 332:853–856 (1988).
Flanegan, J.B. et al., "Tetrahymena Ribozyme Catalyzes Trans–Splicing of Model Oligoribonucleotide Substrates," *J. Cell Biochem. Supp.* 120:28 N202 (1988), Presented at the symposium of the Molecular Biology of RNA Held at the 17th Annual UCLA Symposia on Molecular and Cellular Biology, Keystone, CO (Apr. 1988).
Garriga, G. et al., "Mechanism of recognition of the 5' splice site in self–splicing group 1 introns," *Nature* 322:86–69 (1986).

(List continued on next page.)

Primary Examiner—John L. LaGuyader
Attorney, Agent, or Firm—Sterne, Kessler, Goldstein & Fox P.L.L.C.

[57] ABSTRACT

The design of new ribozymes capable of self-catalyzed trans-splicing which are based upon the catalytic core of a Group I intron are described. Using this design, it is possible to construct ribozymes capable of efficiently splicing a new 3' exon sequence into any chosen target RNA sequence in a highly precise manner. A method of cell ablation is also described that provides a toxic product to a host cell in vivo in a targetted, regulated manner utilizing novel trans-splicing ribozymes of the invention. Inactive pro-ribozyme forms are also described.

11 Claims, 25 Drawing Sheets

OTHER PUBLICATIONS

Haseloff, J. et al., "Simple RNA enzymes with new and highly specific endoribonuclease activities," *Nature* 334:585–591 (1988).

Haseloff, J. et al., "Design of Ribozymes for Trans–Splicing," Presented at The Genome Conference, 13th Annual Conference on the Organisation and Expression of the Genome, Victoria, Australia, Feb. 18–22, 1991, SYM–B–1.

Heus, H.A. et al., "Sequence–dependent structural variations of hammerhead RNA enzymes," *Nucl. Acids Res.* 18(5):1103–1108 (Mar. 1990).

Hirsh, D. et al., "Trans–Splicing and SL RNAs in *C. elegans*," *Mol. Biol. Rpts.* 14(2/3):115 (Mar. 1990).

Hutchins, C.J. et al., "Self–cleavage of plus and minus RNA transcripts of avocado sunblotch viroid," *Nucl. Acids Res.* 14(9):3627–3640 (1986).

James, W., "Toward gene–inhibition therapy: a review of progress and prospects in the field of antiviral antisense nucleic acids and ribozymes," *Antiviral Chem. & Chemotherapy* 2(4):191–214 (Nov. 1991).

Joyce, G.F., "Amplification, mutation and selection of catalytic RNA," *Gene* 82:83–87 (1989).

Kan, N.C. et al., "The intervening sequence of the ribosomal RNA gene is highly conserved between Two Tetrahymena species," *Nucl. Acids Res.* 10(9):2809–2822 (1982).

Keese, P. et al., "The Structure of Viroids and Virusoids," in *Viroids and Viroid–like Pathogens* J.S. Semancik, ed., CRC Press, Boca Raton, Fla. 1987, pp.1–47.

Koizumi, M. et al., "Construction of a series of several self–cleaving RNA duplexes using synthetic 21–mers," *FEBS Letters* 228 (2):228–230 (1988).

Koizumi, M. et al., "Cleavage of specific sites of RNA by designed ribozymes," *FEBS Letters* 239(2):285–288 (1988).

Mariani, C. et al., "Induction of male sterility in plants by a chimaeric ribonuclease gene," *Nature* 347(6295):737–741 (Oct. 1990).

Maxwell, I.H. et al., "Regulated Expression of a Diphtheria Toxin A–Chain Gene Transfected into Human Cells: Possible Strategy for Inducing Cancer Cell Suicide," *Cancer Research* 46:4660–4664.

Michel, F. et al., "The guanosine binding site of the Tetrahymena ribozyme," *Nature* 342:391–395 (1989).

Mulligan, R.C. et al., "The Basic Science of Gene Therapy," *Science* 260:926–932 (1993).

Palmiter, R.D. et al., "Cell Lineage Ablation in Transgenic Mice by Cell–Specific Expression of a Toxin Gene," *Cell* 50:435–443 (1987).

Qian, S. et al., "Antisense ribosomal protein gene expression specifically disrupts oogenesis in *Drosophila melanogaster*," *Proc. Natl. Acad. Sci. USA* 85:9601–9605 (1988).

Reiss, B. et al., "Protein fusions with the kanamycin resistance gene from transposon Tn5," *EMBO J.* 3:(13):3317–3322 (1984).

Riedel, C.J. et al., "Diphtheria toxin mutant selectively kills cerebellar purkinje neurons," *Proc. Natl. Acad. Sci. USA* 87:5051–5055 (Jul. 1990).

Salvo, J.L.G. et al., "Deletion–tolerance and Trans–splicing of the Bacteriophage T4 TD Intron," *J. Mol. Biol.* 211(3):537–549 (Feb. 1990).

Sarver, N. et al., "Ribozymes as Potential Anti–HIV–1 Therapeutic Agents," *Science* 247(4947):1222–1225 (Mar. 1990).

Suh, E.R. et al., "Base Pairing between the 3' Exon and an Internal Guide Sequence Increases 3' Splice Site Specificity in the Tetrahymena Self–Splicing rRNA Intron," *Mol. Cell. Biol.* 10(6):2960–2965 (Jun. 1990).

Szostak, J.W., "Enzymatic activity of the conserved core of a group I self–splicing intron," *Nature* 322:83–86 (1986).

Taira, K. et al., "Construction of a novel artificial–ribozyme–releasing plasmid," *Protein Engineering* 3(8):733–737 (Aug. 1990).

Walbot, V. et al., "Plant development and ribozymes for pathogens," *Nature* 334:196–197 (1988).

Waring, R.B. et al., "The Tetrahymena rRNA Intron Self–Splices in *E. Coli*: In Vivo Evidence for the Importance of Key Base–Paired Regions of RNA for RNA Enzyme Function," *Cell* 40:371–380 (1985).

Wert, S.E. et al., "Morphological Analysis of Lung Cell Ablation in Transgenic Mice Expressing a Toxic Fusion Gene," *Am. Rev. Respir. Dis.* 141(No. 4, Pt2):A695 (Apr. 1990).

Winter, A.J. et al., "The mechanism of Group I self–splicing: an internal guide sequence can be provided in Tans," *EMBO J.* 9(6):1923–1928 (Jun. 1990).

M. Morl et al., Cell 60 ('90) 629–36.

W. James, Anti–viv Chem. & Chemothu. 2(4) ('91) 191–214.

M. Goldman et al., EMBO J., vol.13 ('94) 2976–84.

D. Ornitz et al. PNAS 88 ('91) 698–702.

Brunvand, M.W., et al., "Nuclear Factors Interacting with the Mitogen–responsive Regulatory Region of the Interleukin–2 Gene," *J. Biol. Chem.* 263(35):18904–18901 (1988).

Lake, R. A. et al., "A 3' transcriptional enhancer regulates tissue–specific expression of the human CD2 gene," *EMBO J.* 9(10):3129–3136 (Oct. 1990).

Maniatis, T., et al., "Regulation of inducible and tissue–specific gene expression," *Science* 236:1237 (1987), Full text of article as obtained from DIALOG file 149 (IAC(SM) Health & Wellness DB(SM)),19 pages.

Morohashi, K.–i., and Omura, T., "Tissue–Specific Transcription of P–450(11β) Gene In Vitro," *J. Biochem.* 108:1050–1056 (Dec. 1990).

Pierani, A., et al., "Activation of Octamer–Containing Promoters by Either Octamer–Binding Transcription Factor 1 (OTF–1) or OTF–2 and Requirement of an Additional B–Cell–Specific Component for Optimal Transcription of Immunoglobulin Promoters," *Mol. Cell. Biol.* 10(12):6204–6215 (Dec. 1990).

Sartorelli, V., et al., "Muscle–specific expression of the cardiac α–actin gene requires MyoD1, CArG–box binding factor, and Sp1," *Genes and Development* 4:1811–1822 (Oct. 1990).

Sternberg, E.A., et al., "Identification of Upstream and Intragenic Regulatory Elements That Confer Cell–Type–Restricted and Differentiation–Specific Expression on the Muscle Creating Kinase Gene," *Mol. Cell. Biol.* 8(7):2896–2909 (1988).

Trainor, C., et al., "Structure and evolution of a human erythroid transcription factor," *Nature* 343:92–96 (Jan. 1990).

Yamamoto, M., et al., "Activity and tissue–specific expression of the transcription factor NF–E1 multigene family," *Genes and Development* 4:1650–1662 (Oct. 1990).

Yoza, B.K., and Roeder, R.G., "Identification of a Novel Factor That Interacts with an Immunoglobulin Heavy–Chain Promoter and Stimulates Transcription in Conjunction with the Lymphoid Cell–Specific Factor OTF2," *Mol. Cel. Biol.* 10(5):2145–2153 (May 1990).

1. GUANOSINE-MEDIATED CLEAVAGE OF 5' SPLICE SITE.
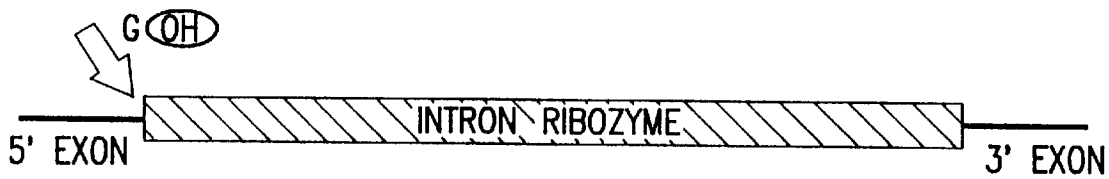
2. CLEAVAGE OF 3' SPLICE SITE.
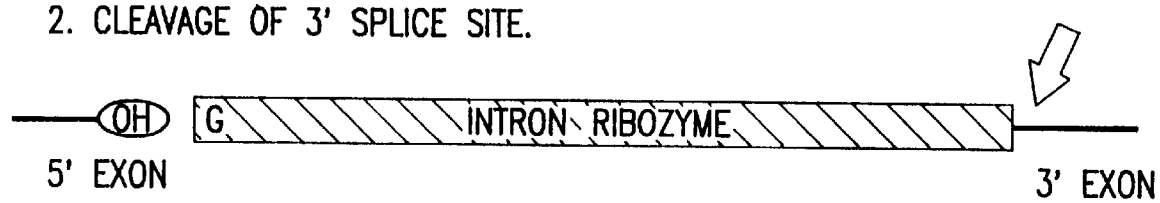
3. LIGATION OF EXON SEGMENTS.
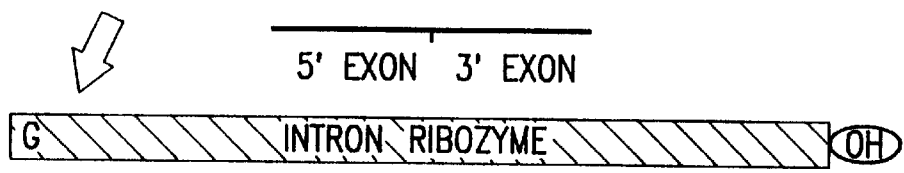
4. CIRCULARIZATION OF INTRON.
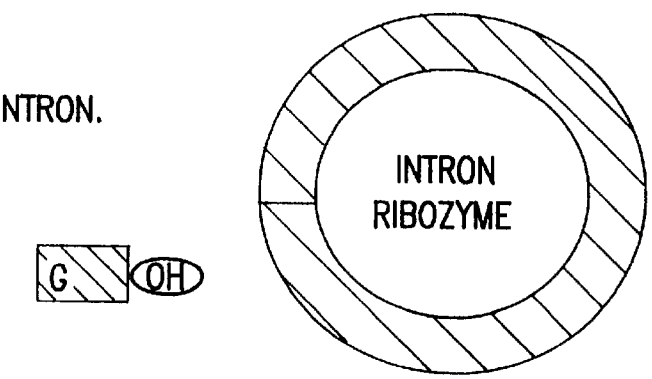
FIG.1

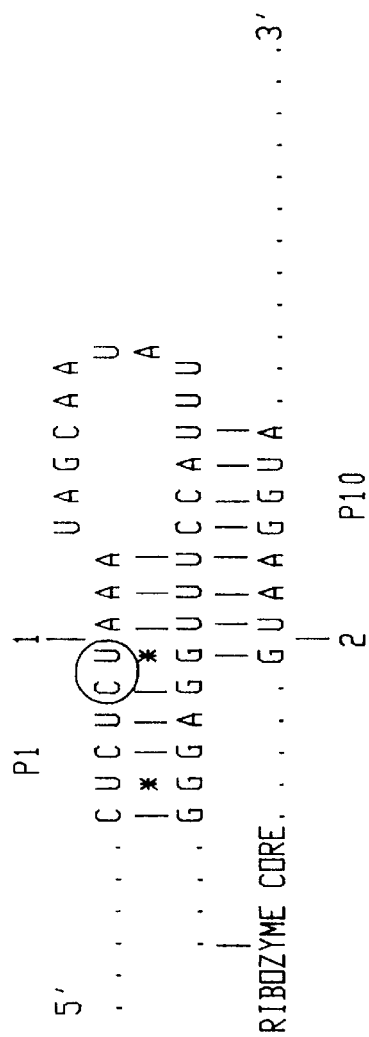
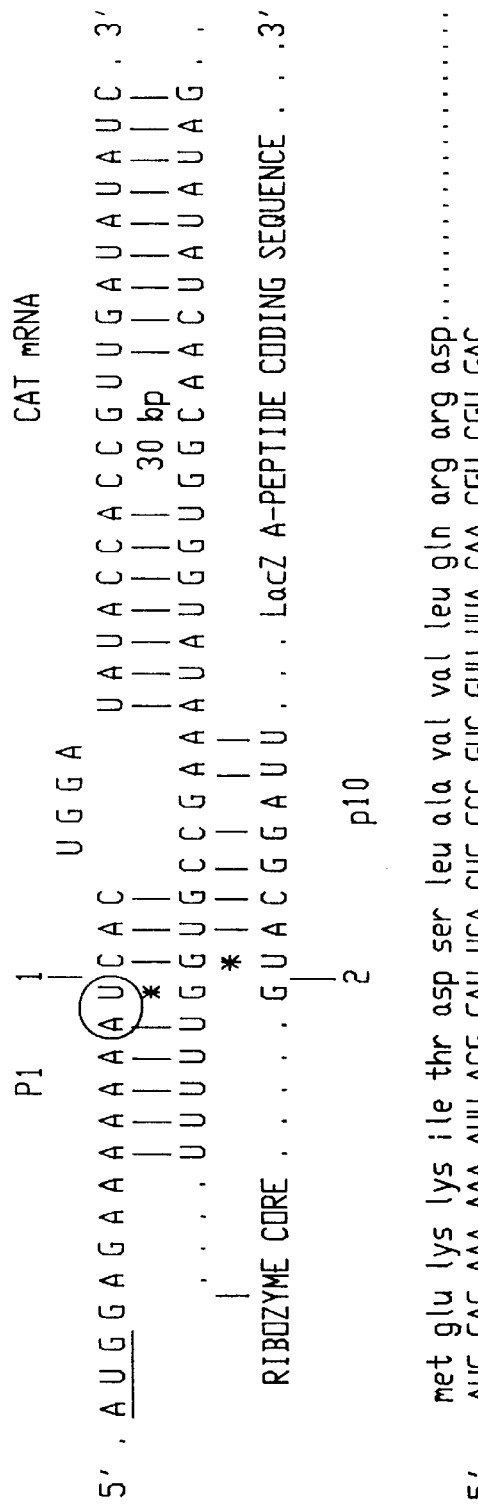
FIG. 3A

```
  1 GGGAGACCGG AAGCTTCTTT ACGATGCCAT TGGGATATAT CAACGGTGGT ATAAAGCCGT  60
 61 GGTTTTAAAA AGTTATCAGG CATGCACCTG GTAGCTAGTC TTTAAACCAA TAGATTGCAT 120
121 CGGTTAAAAA GGCAAGACCG TCAAATTGCG GGAAAGGGGT CAACAGCCGT TCAGTACCAA 180
181 GTCTCAGGGG AAACTTTGAG ATGGCCTTGC AAAGGGTATG GTAATAAGCT GACGGACATG 240
241 GTCCTAACCA CGCAGCCAAG TCCTAAGTCA ACAGATCTTC TGTTGATATG GATGCAGTTC 300
301 ACAGACTAAA TGTCGGTCGG GGAAGATGTA TTCTTCTCAT AAGATATAGT CGGACCTCTC 360
361 CTTAATGGGA GCTAGCGGAT GAAGTGATGC AACACTGGAG CCGCTGGGAA CTAATTGTA  420
421 TGGGAAAGTA TATTGATTAG TTTTGGAGTA CTCGTACGGA TTCACTGGCC GTCGTTTTAC 480
481 AACGTCGTGA CTGGAAAAAC CCTGGCGTTA CCCAACTTAA TCGCCTTGCA GCACATCCCC 540
541 CTTTCGCCAG CTGGCGTAAT AGCGAAGAGG CCCGCACCGA TCGCCCTTCC CAACAGTTGC 600
601 GCAGCCTGAA TGGAAATTGT AAG                                         623
       |          |          |          |          |          |
      10         20         30         40         50         60
```

FIG.3B

CMV isolates.

```
WD   UUUGCGUCU.......UAGUGUGCCU  AUG GAC AAA U.CU GGA U.CU CCC AAU GCU AGU
Q    UUUGCGUCUCAG......UGUGCCU   AUG GAC AAA U.CU GGA U.CU CCC AAU GCU AGU
Fny  UUUGUGUCGUAGAAUUGAGUCGAGUC  AUG GAC AAA U.CU GGA U.CU ACC AGU GCU GGU
M    UUUGUGUCGUAGAAUUGAGUCGAGUC  AUG GAU AAA U.CU GAA U.CA ACC AGU GCU GGU
I    UUUGUGUCGUAGAAUUGAGUCGAGUC  AUG GAC AAA U.CU GAA U.CA ACC AGU GCU GGU
O    UUUACGUCGUAGAAUUGAGUCGAGUC  AUG GAC AAA U.CU GAA U.CA ACC AGU GCU GGU
Y    UUUGUGUCGUAGAAUUGAGUCGAGUC  AUG GAC AAA U.CU GAA U.CA ACC AGU GCU GGU
D    UUUGUGUCGUAGAAUUGAGUCGAGUC  AUG GAC AAA U.CU GAA U.CA ACC AGU GCU GGU
C    UUUGUGUCGUAGAAUUGAGUCGAGUC  AUG GAC AAA U.CU GAA U.CA ACC AGU GCU GGU
                                     1           1                  2
5'                                                                        3'
```

FIG. 4A

```
          1              2
5' AATTTTGTGTCGTAGAATTGAGTCGAGTC ATG GAC AAA T.CT GAA T.CA ACC AGT GCT GCA  3'
   ||||||||||||||||||||||||||||| ||| ||| ||| |||| ||| |||| ||| ||| ||| ||
   AACACAGCATCTTAACTCAGCTCAG TAC CTG TTT A.GA CTT A.GT TGG TCA GC   5' PstI
   EcoRI
```

FIG. 4B

Ribozyme 1

```
5'AAUUUGUGUCGUAGAAUUGAGUCAUGGACAAAU.CUGAAUCAACCAGUGCUGCA 3'
                      |||||*  ||||      ||||||||| (41 bp)
             ........UGUUUG  GACUACUAUGGUUACGA  ... 5'
                                            *|||||||****
             RIBOZYME CORE........G.UUGAUGAUAGGUACCUCGAUGAUGUUGUUGAU... 3'
                           |
                           1
met asp lys phe asp asp arg tyr leu asp asp val ser....
AUG GAC AAA UUU GAU GAU AGG UAC CUC GAU GAU GUU UCU...3'
```

Ribozyme 2

```
5'AAUUUGUGUCGUAGAAUUGAGUCGAGUCAUGGACAAAUCUGAAU.CAACCAGUGCUGCA 3'
                             |||||* |||      |||  (46 bp)
                     ........GACUUG GUUCCUACCGA ... 5'
                                              *|||*|||
             RIBOZYME CORE........G.UAAGGGUGGGGUACCUCGAUGAUGUUGUUGAU... 3'
                           |
                           2
met asp lys ser glu leu arg val gly tyr leu asp asp....
AUG GAC AAA UCU GAA UUA AGG GUG GGG UAC CUC GAU GAU...3'
```

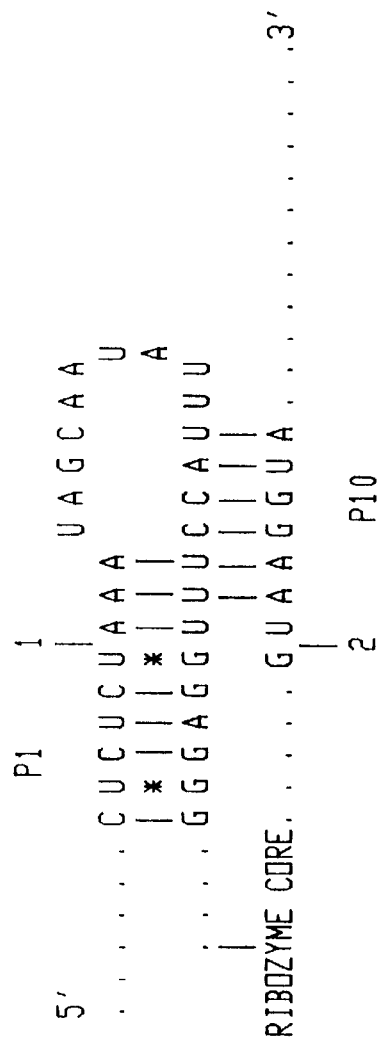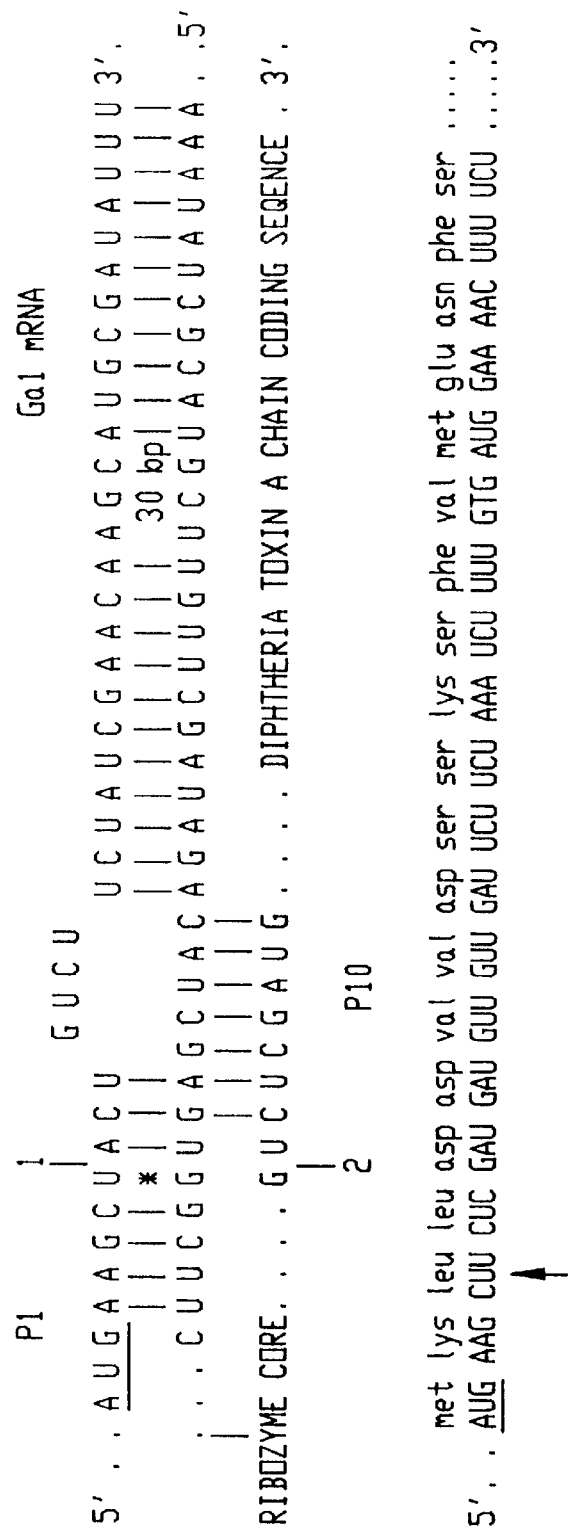
FIG.6A

```
                10         20         30         40         50         60
  1  GTCGACCTTT TTAAGTCGGC AAATATCGCA TGTTTGTTCG ATAGACATCG AGTGGCTTCA   60
 61  AAAGTTATCA GGCATGCACC TGGTAGCTAG TCTTAAACC AATAGATTGC ATCGGTTTAA  120
121  AAGGCAAGAC CGTCAAATTG CGGGAAAGGG GTCAACAGCC AAGTCTCAGG            180
181  GGAAACTTTG AGATGGCCTT AGATCCTAAGT TGGTAATAAG CTGACGTACC TGGTCCTAAC  240
241  CACGCAGCCA AGTCCTAAGT CAACAGATCT TCTGTTGATA TGGATGCAGT TCACAGACTA  300
301  AATGTCGGTC GGGGAAGATG TATTCTTCTC ATAAGATATA GTCGGACCTC TCCTTAATGG  360
361  GAGCTAGCGG ATGAAGTGAT GCAACACTGG AGCCGCTGGG AACTAATTTG TATGCGAAAG  420
421  TATATTGATT AGTTTGGAG TACTCGTCTC GATGATGTTG TTGATTCTTC TAAATCTTTT  480
481  GTGATTGAAA ACTTTTCTTC GTACCACGGG ACTAAACCTG GTTATGTAGA TTCCATTCAA  540
541  AAAGGTATAC AAAAGCCAAA ATCTGGTACA CAAGGAAATT ATGACGATGA TTGGAAAGGG  600
601  TTTTATAGTA CCGACAATAA ATACGACGCT GCGGGATACT CTGTAGATAA TGAAAACCCG  660
661  CTCTCTGGAA AAGCTGGAGG CGTGGTCAAA GTGACGTATC CAGGACTGAC GAAGGTTCTC  720
721  GCACTAAAAG TGGATAATGC CGAAACTATT AAGAAAGAGT TAGGTTTAAG TCTCACTGAA  780
781  CCGTTGATGG AGCAAGTCGG AACGGAAGAG TTTATCAAAA GGTTCGGTGA TGGTGCTTCG  840
841  CGTGTAGTGC TCAGCCTTCC CTTCGCTGAG GGGAGTTCTA GCGTTGAATA TATTAATAAC  900
901  TGGGAACAGG TCAAAGCGTT AAGCGTAGAA CTTGAGATTA ATTTGAAAC CCGTGGAAAA  960
961  CGTGGCCAAG ATGCGATGTA TGAGTATATG GCTCAAGCCT GTGCAGGAAA TCGTGTCAGG 1020
1021 CGATCTTTGT GACTCGAG                                                1038
```

FIG. 6B

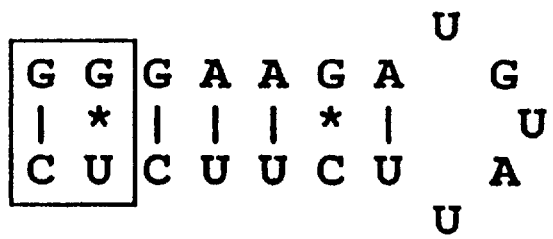
13 nt
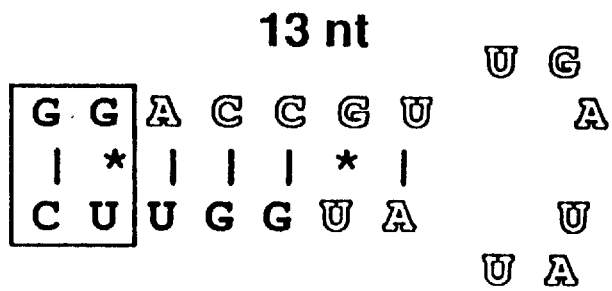
18 nt
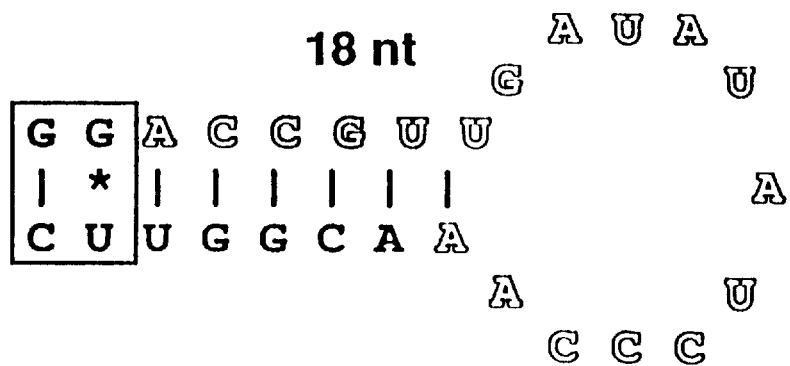
N = complementary to "anti-sense"
FIG. 13C

Wild-type
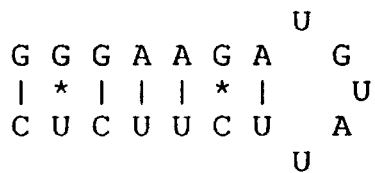
GAL4-DTA pro-ribozyme 1
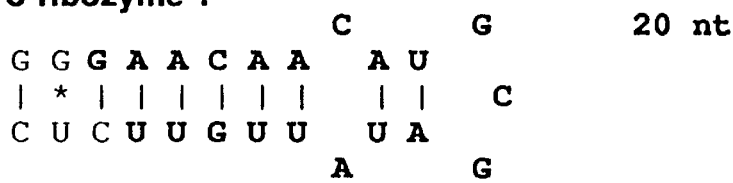
20 nt
CAT-LacZ pro-ribozyme 1
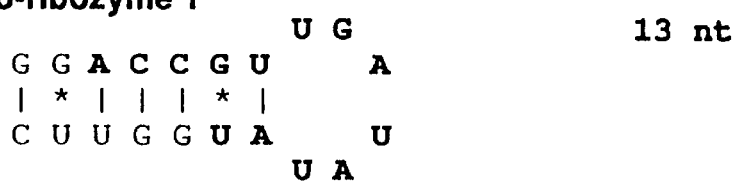
13 nt
CAT-LacZ pro-ribozyme 2
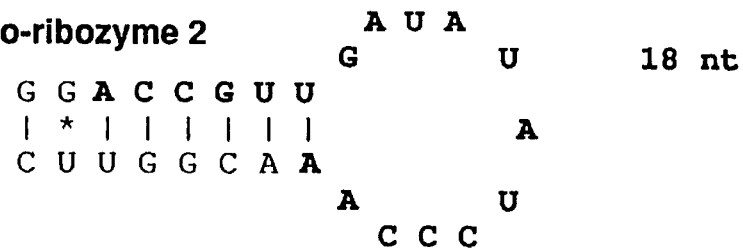
18 nt
GAL4-DTA pro-ribozyme 2
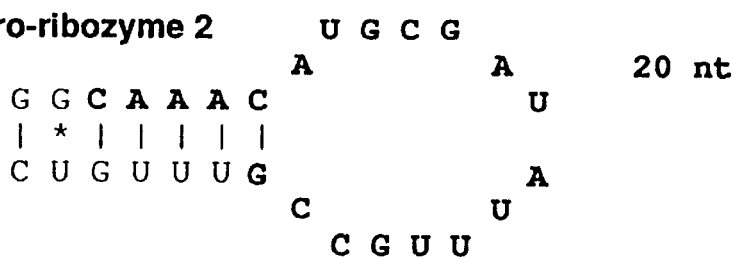
20 nt
N = complementary to ribozyme "anti-sense"
FIG. 17

2

SEQUENCE LISTING ( 1 ) GENERAL INFORMATION:

( i i i ) NUMBER OF SEQUENCES: 56

( 2 ) INFORMATION FOR SEQ ID NO:1:

( i ) SEQUENCE CHARACTERISTICS:
        ( A ) LENGTH: 517 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:1:

```
TGACGCAATT   CAACCAAGCG   CGGGTAAACG   GCGGGAGTAA   CTATGACTCT   CTAAATAGCA         60

ATATTTACCT   TTGGAGGGAA   AAGTTATCAG   GCATGCACCT   CCTAGCTAGT   CTTTAAACCA        120

ATAGATTGCA   TCGGTTTAAA   AGGCAAGACC   GTCAAATTGC   GGGAAAGGGG   TCAACAGCCG        180

TTCAGTACCA   AGTCTCAGGG   GAAACTTTGA   CATGGCCTTG   CAAAGGGTAT   GGTAATAAGC        240

TGACGGACAT   GGTCCTAACC   ACGCAGCCAA   GTCCTAAGTC   AACAGATCTT   CTGTTGATAT        300

GGATGCAGTT   CACAGACTAA   ATGTCGGTCG   GGGAAGATGT   ATTCTTCTCA   TAAGATATAG        360

TCGGACCTCT   CCTTAATGGG   AGGTAGCGGA   TGAATGGATG   CAACACTGGA   GCCGCTGGGA        420

ACTAATTTGT   ATGCGAAAGT   ATATTGATTA   GTTTTGGAGT   ACTCGTAAGG   TAGCCAAATG        480

CCTCGTCATC   TAATTAGTGA   CGCGCATGAA   TGGATTA                                    517
```

( 2 ) INFORMATION FOR SEQ ID NO:2:

( i ) SEQUENCE CHARACTERISTICS:
        ( A ) LENGTH: 82 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:2:

```
GGCCAAGCTT   CTTTACGATG   CCATTGGGAT   ATATCAACGG   TGGTATAAAC   CCGTGGTTTT         60

TAAAAGTTAT   CAGGCATGCA   CC                                                        82
```

( 2 ) INFORMATION FOR SEQ ID NO:3:

( i ) SEQUENCE CHARACTERISTICS:
        ( A ) LENGTH: 47 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:3:

```
GATTAGTTTT   GGAGTACTCG   TACGGATTCA   CGGCCGTCGT   TTTACAA                         47
```

( 2 ) INFORMATION FOR SEQ ID NO:4:

( i ) SEQUENCE CHARACTERISTICS:
        ( A ) LENGTH: 43 base pairs (B) TYPE: nucleic acid
(C) STRANDEDNESS: both
(D) TOPOLOGY: linear (xi) SEQUENCE DESCRIPTION: SEQ ID NO:4:

| | | | | | |
|---|---|---|---|---|---|
| GGCCGAATTC | TTACAATTTC | CATTCAGGCT | GCGCAACTGT | TGG | 43 |

(2) INFORMATION FOR SEQ ID NO:5:

(i) SEQUENCE CHARACTERISTICS:
(A) LENGTH: 623 base pairs
(B) TYPE: nucleic acid
(C) STRANDEDNESS: both
(D) TOPOLOGY: linear (xi) SEQUENCE DESCRIPTION: SEQ ID NO:5:

| | | | | | |
|---|---|---|---|---|---|
| GGGAGACCGG | AAGCTTCTTT | ACGATGCCAT | GGGATATAT | CAACGGTGGT | ATAAAGCCGT | 60 |
| GGTTTTTAAA | AGTTATCAGG | CATGCACCTG | GTAGCTAGTC | TTTAAACCAA | TAGATTGCAT | 120 |
| CGGTTTAAAA | GGCAAGACCG | TCAAATTGCG | GGAAAGGGGT | CAACAGCCGT | TCAGTACCAA | 180 |
| GTCTCAGGGG | AAACTTTGAG | ATGGCTTGC | AAAGGGTATG | GTAATAAGCT | GACGGACATG | 240 |
| GTCCTAACCA | CGCAGCCAAG | TCCTAAGTCA | ACAGATCTTC | TGTTGATATG | GATGCAGTTC | 300 |
| ACAGACTAAA | TGTCGGTCGG | GGAAGATGTA | TTCTTCTCAT | AAGATATAGT | CGGACCTCTC | 360 |
| CTTAATGGGA | GCTAGCGGAT | GAAGTGATGC | AACACTGGAG | CCGCTGGGAA | CTAATTTGTA | 420 |
| TGCGAAAGTA | TATTGATTAG | TTTTGGAGTA | CTCGTACGGA | TTCACTGGCC | GTCGTTTAC | 480 |
| AACGTCGTGA | CTGGGAAAAC | CCTGGCGTTA | CCCAACTTAA | TCGCCTTGCA | GCACATCCCC | 540 |
| CTTTCGCCAG | CTGGCGTAAT | AGCGAAGAGG | CCCGCACCGA | TCGCCCTTCC | CAACAGTTGC | 600 |
| GCAGCCTGAA | TGGAAATTGT | AAG | | | | 623 |

(2) INFORMATION FOR SEQ ID NO:6:

(i) SEQUENCE CHARACTERISTICS:
(A) LENGTH: 1038 base pairs
(B) TYPE: nucleic acid
(C) STRANDEDNESS: both
(D) TOPOLOGY: linear (xi) SEQUENCE DESCRIPTION: SEQ ID NO:6:

| | | | | | |
|---|---|---|---|---|---|
| GTCGACCTTT | TTAAGTCGGC | AAATATCGCA | TGTTTGTTCG | ATAGACATCG | AGTGGCTTCA | 60 |
| AAAGTTATCA | GGCATGCACC | TGGTAGCTAG | TCTTTAAACC | AATAGATTGC | ATCGGTTTAA | 120 |
| AAGGCAAGAC | CGTCAAATTG | CGGGAAAGGG | GTCAACAGCC | GTTCAGTACC | AAGTCTCAGG | 180 |
| GGAAACTTTG | AGATGGCCTT | GCAAAGGGTA | TGGTAATAAG | CTGACGGACA | TGGTCCTAAC | 240 |
| CACGCAGCCA | AGTCCTAAGT | CAACAGATCT | TCTGTTGATA | TGGATGCAGT | TCACAGACTA | 300 |
| AATGTCGGTC | GGGGAAGATG | TATTCTTCTC | ATAAGATATA | GTCGGACCTC | TCCTTAATGG | 360 |
| GAGCTAGCGG | ATGAAGTGAT | GCAACACTGG | AGCCGCTGGG | AACTAATTTG | TATGCGAAAG | 420 |
| TATATTGATT | AGTTTTGGAG | TACTCGTCTC | GATGATGTTG | TTGATTCTTC | TAAATCTTTT | 480 |
| GTGATTGAAA | ACTTTTCTTC | GTACCACGGG | ACTAAACCTG | GTTATGTAGA | TTCCATTCAA | 540 |
| AAAGGTATAC | AAAAGCCAAA | ATCTGGTACA | CAAGGAAATT | ATGACGATGA | TTGGAAAGGG | 600 |
| TTTTATAGTA | CCGACAATAA | ATACGACGCT | GCGGGATACT | CTGTAGATAA | TGAAAACCCG | 660 |
| CTCTCTGGAA | AAGCTGGAGG | CGTGGTCAAA | GTGACGTATC | CAGGACTGAC | GAAGGTTCTC | 720 |
| GCACTAAAAG | TGGATAATGC | CGAAACTATT | AAGAAAGAGT | TAGGTTTAAG | TCTCACTGAA | 780 |
| CCGTTGATGG | AGCAAGTCGG | AACGGAAGAG | TTTATCAAAA | GGTTCGGTGA | TGGTGCTTCG | 840 |

```
CGTGTAGTGC  TCAGCCTTCC  CTTCGCTGAG  GGGAGTTCTA  GCGTTGAATA  TATTAATAAC       900

TGGGAACAGG  CGAAAGCGTT  AAGCGTAGAA  CTTGAGATTA  ATTTTGAAAC  CCGTGGAAAA       960

CGTGGCCAAG  ATGCGATGTA  TGAGTATATG  GCTCAAGCCT  GTGCAGGAAA  TCGTGTCAGG      1020

CGATCTTTGT  GACTCGAG                                                        1038
```

( 2 ) INFORMATION FOR SEQ ID NO:7:

( i ) SEQUENCE CHARACTERISTICS:
        ( A ) LENGTH: 134 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:7:

```
GTTTAGTTGT  TCACCTGAGT  CGTGTGTTTT  GTATTTGCG  TCTTAGTGTG  CCTATGGACA        60

AATCTGGATC  TCCCAATGCT  AGTAGAACCT  CCCGGCGTCG  TCGCCCGCGT  AGAGGTTCTC      120

GGTCCGCTTC  TGGT                                                             134
```

( 2 ) INFORMATION FOR SEQ ID NO:8:

( i ) SEQUENCE CHARACTERISTICS:
        ( A ) LENGTH: 134 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:8:

```
GTTTAGTTGT  TCACCTGAGT  CGTGTTTTCT  TTGTTTTGCG  TCTCAGTGTG  CCTATGGACA       60

AATCTGGATC  TCCCAATGCT  AGTAGAACCT  CCCGGCGTCG  TCGCCCGCGT  AGAGGTTCTC      120

GGTCCGCTTC  TGGT                                                             134
```

( 2 ) INFORMATION FOR SEQ ID NO:9:

( i ) SEQUENCE CHARACTERISTICS:
        ( A ) LENGTH: 152 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:9:

```
GTTATTGTCT  ACTGACTATA  TAGAGAGTGT  TTGTGCTGTG  TTTTCTCTTT  TGTGTCGTAG       60

AATTGAGTCG  AGTCATGGAC  AAATCTGAAT  CAACCAGTGC  TGGTCGTAAC  CGTCGACGTC      120

GTCCGCGTCG  TGGTTCCCGC  TCCGCCCCCT  CC                                       152
```

( 2 ) INFORMATION FOR SEQ ID NO:10:

( i ) SEQUENCE CHARACTERISTICS:
        ( A ) LENGTH: 152 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:10:

```
GTTATTGTCT  ACTGACTATA  TAGAGAGTGT  GTGTGCTGTG  TTTTCTCTTT  TGTGTCGTAG       60

AATTGAGTCG  AGTCATGGAT  AAATCTGAAT  CAACCAGTGC  TGGTCGTAAC  CGTCGACGTC      120

GTCCGCGTCG  TGGTTCCCGC  TCCGCCTCCT  CC                                       152
```

( 2 ) INFORMATION FOR SEQ ID NO:11:

( i ) SEQUENCE CHARACTERISTICS:

(A) LENGTH: 131 base pairs
(B) TYPE: nucleic acid
(C) STRANDEDNESS: both
(D) TOPOLOGY: linear (xi) SEQUENCE DESCRIPTION: SEQ ID NO:11:

| | | | | | |
|---|---|---|---|---|---|
| AGAGAGTGTG | TGTGCTGTGT | TTTCTCTTTT | GTGTCGTAGA | ATTGAGTCGA | GTCATGGACA | 60
| AATCTGAATC | AACCAGTGCT | GGTCGTAACC | GTCGACGTCG | TCCGCGTCGT | GGTTCCCGCT | 120
| CCGCCCCTC | C | | | | | 131

(2) INFORMATION FOR SEQ ID NO:12:

(i) SEQUENCE CHARACTERISTICS:
(A) LENGTH: 154 base pairs
(B) TYPE: nucleic acid
(C) STRANDEDNESS: both
(D) TOPOLOGY: linear (xi) SEQUENCE DESCRIPTION: SEQ ID NO:12:

| | | | | | |
|---|---|---|---|---|---|
| GTTATTGTCT | ACTGATTGTA | TAAAGAGTGT | GTGTGTGCTG | TGTTTTCTCT | TTTACGTCGT | 60
| AGAATTGAGT | CGAGTCATGG | ACAAATCTGA | ATCAACCAGT | GCTGGTCGCA | ACCGTCGACG | 120
| TCGTCCGCGT | CGTGGTTCCC | GCTCCGCCCC | CTCC | | | 154

(2) INFORMATION FOR SEQ ID NO:13:

(i) SEQUENCE CHARACTERISTICS:
(A) LENGTH: 154 base pairs
(B) TYPE: nucleic acid
(C) STRANDEDNESS: both
(D) TOPOLOGY: linear (xi) SEQUENCE DESCRIPTION: SEQ ID NO:13:

| | | | | | |
|---|---|---|---|---|---|
| GTTATTGTCT | ACTGACTATA | TAGAGAGTGT | GTGTGTGCTG | TGTTTTCTCT | TTTGTGTCGT | 60
| AGAATTGAGT | CGAGTCATGG | ACAAATCTGA | ATCAACCAGT | GCTGGTCGTA | ACCGTCGACG | 120
| TCGTTTGCGT | CGTGGTTCCC | GCTCCGCCTC | CTCC | | | 154

(2) INFORMATION FOR SEQ ID NO:14:

(i) SEQUENCE CHARACTERISTICS:
(A) LENGTH: 130 base pairs
(B) TYPE: nucleic acid
(C) STRANDEDNESS: both
(D) TOPOLOGY: linear (xi) SEQUENCE DESCRIPTION: SEQ ID NO:14:

| | | | | | |
|---|---|---|---|---|---|
| GAGTGTGTAT | GTGCTGTGTT | TTCTCTTTTG | TGTCGTAGAA | TTGAGTCGAG | TCATGGACAA | 60
| ATCTGAATCA | ACCAGTGCTG | GTCGTAACCG | TCGACGTCGT | CCGCGTCGTG | GTTCCCGCTC | 120
| CGCCCCCTCC | | | | | | 130

(2) INFORMATION FOR SEQ ID NO:15:

(i) SEQUENCE CHARACTERISTICS:
(A) LENGTH: 152 base pairs
(B) TYPE: nucleic acid
(C) STRANDEDNESS: both
(D) TOPOLOGY: linear (xi) SEQUENCE DESCRIPTION: SEQ ID NO:15:

| | | | | | |
|---|---|---|---|---|---|
| GTTATTGTCT | ACTGACTATA | TAGAGAGTGT | GTGTGCTGTG | TTTTCTCTTT | TGTGTCGTAG | 60
| AATTGAGTCG | AGTCATGGAC | AAATCTGAAT | CAACCAGTGC | TGGTCGTAAC | CATCGACGTC | 120
| GTCCGCGTCG | TGGTTCCCGC | TCCGCCCCT | CC | | | 152

( 2 ) INFORMATION FOR SEQ ID NO:16:

( i ) SEQUENCE CHARACTERISTICS:
        ( A ) LENGTH: 78 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:16:

GGAGGGGGCG GAGCGGGAAC CACGACGCGG ACGACGTCGA CGGTTACGAC CAGCCCTGGT    60

AGATTCAGAT TTGTCCAT    78

( 2 ) INFORMATION FOR SEQ ID NO:17:

( i ) SEQUENCE CHARACTERISTICS:
        ( A ) LENGTH: 49 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:17:

TTTGCGTCTT AGTGTGCCTA TGGACAAATC TGGATCTCCC AATGCTAGT    49

( 2 ) INFORMATION FOR SEQ ID NO:18:

( i ) SEQUENCE CHARACTERISTICS:
        ( A ) LENGTH: 49 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:18:

TTTGCGTCTC AGTGTGCCTA TGGACAAATC TGGATCTCCC AATGCTAGT    49

( 2 ) INFORMATION FOR SEQ ID NO:19:

( i ) SEQUENCE CHARACTERISTICS:
        ( A ) LENGTH: 56 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:19:

TTTGTGTCGT AGAATTGAGT CGAGTCATGG ACAAATCTGA ATCAACCAGT GCTGGT    56

( 2 ) INFORMATION FOR SEQ ID NO:20:

( i ) SEQUENCE CHARACTERISTICS:
        ( A ) LENGTH: 56 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:20:

TTTGTGTCGT AGAATTGAGT CGAGTCATGG ATAAATCTGA ATCAACCAGT GCTGGT    56

( 2 ) INFORMATION FOR SEQ ID NO:21:

( i ) SEQUENCE CHARACTERISTICS:
        ( A ) LENGTH: 56 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:21:

TTTGTGTCGT AGAATTGAGT CGAGTCATGG ACAAATCTGA ATCAACCAGT GCTGGT    56

( 2 ) INFORMATION FOR SEQ ID NO:22:

( i ) SEQUENCE CHARACTERISTICS:
        ( A ) LENGTH: 56 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:22:

TTTACGTCGT AGAATTGAGT CGAGTCATGG ACAAATCTGA ATCAACCAGT GCTGGT    56

( 2 ) INFORMATION FOR SEQ ID NO:23:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

TTTGTGTCGT AGAATTGAGT CGAGTCATGG ACAAATCTGA ATCAACCAGT GCTGGT    56

( 2 ) INFORMATION FOR SEQ ID NO:24:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

TTTGTGTCGT AGAATTGAGT CGAGTCATGG ACAAATCTGA ATCAACCAGT GCTGGT    56

( 2 ) INFORMATION FOR SEQ ID NO:25:

( i ) SEQUENCE CHARACTERISTICS:
        ( A ) LENGTH: 56 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:25:

TTTGTGTCGT AGAATTGAGT CGAGTCATGG ACAAATCTGA ATCAACCAGT GCTGGT    56

( 2 ) INFORMATION FOR SEQ ID NO:26:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:26:

AATTTTGTGT CGTAGAATTG AGTCGAGTCA TGGACAAATC TGAATCAACC AGTGCTGCA    59

( 2 ) INFORMATION FOR SEQ ID NO:27:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:27:

GCACTGGTTG ATTCAGATTT GTCCATGACT CGACTCAATT CTACGACACA A    51

( 2 ) INFORMATION FOR SEQ ID NO:28:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:28:

AATTTTGTGT CGTAGAATTG AGTCGAGTCA TGGACAAATC TGAATCAACC AGTGCTGCA    59

( 2 ) INFORMATION FOR SEQ ID NO:29:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:29:

AGCATTGGTA TCATCAGGTT TGT    23

( 2 ) INFORMATION FOR SEQ ID NO:30:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:30:

GTTGATGATG TTGTTGATTC T    21

( 2 ) INFORMATION FOR SEQ ID NO:31:

( i ) SEQUENCE CHARACTERISTICS:
        ( A ) LENGTH: 10 amino acids
        ( B ) TYPE: amino acid
        ( D ) TOPOLOGY: linear ( x i ) SEQUENCE DESCRIPTION: SEQ ID NO:31:

Met Asp Lys Phe Asp Asp Val Val Asp Ser
1               5                        10

( 2 ) INFORMATION FOR SEQ ID NO:32:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:32:

ATGGACAAAT TTGATGATGT TGTTGATTCT    30

( 2 ) INFORMATION FOR SEQ ID NO:33:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:33:

AATTTTGTGT CGTAGAATTG AGTCGAGTCA TGGACAAATC TGAATCAACC AGTGCTGCA    59

( 2 ) INFORMATION FOR SEQ ID NO:34:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:34:

AGCCATCCTT GGTTCAG 17

( 2 ) INFORMATION FOR SEQ ID NO:35:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:35:

GTAAGGGTGG ATGTT 15

( 2 ) INFORMATION FOR SEQ ID NO:36:

( i ) SEQUENCE CHARACTERISTICS:
( A ) LENGTH: 10 amino acids
( B ) TYPE: amino acid
( D ) TOPOLOGY: linear ( x i ) SEQUENCE DESCRIPTION: SEQ ID NO:36:

Met Asp Lys Ser Glu Leu Arg Val Asp Val
1               5                   10

( 2 ) INFORMATION FOR SEQ ID NO:37:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( x i ) SEQUENCE DESCRIPTION: SEQ ID NO:37:

ATGGACAAAT CTGAATTAAG GGTGGATGTT 30

( 2 ) INFORMATION FOR SEQ ID NO:38:

( i ) SEQUENCE CHARACTERISTICS:
( A ) LENGTH: 70 base pairs
( B ) TYPE: nucleic acid
( C ) STRANDEDNESS: single
( D ) TOPOLOGY: linear ( x i ) SEQUENCE DESCRIPTION: SEQ ID NO:38:

TCTCGATGAT GTTGTTGATT CTTCTAAATC TTTTGTGATG GAAAACTTTT CTTCGTACCA 60

CGGGACTAAA 70

( 2 ) INFORMATION FOR SEQ ID NO:39:

( i ) SEQUENCE CHARACTERISTICS:
( A ) LENGTH: 11 amino acids
( B ) TYPE: amino acid
( D ) TOPOLOGY: linear ( x i ) SEQUENCE DESCRIPTION: SEQ ID NO:39:

Met Glu Asn Phe Ser Ser Tyr His Gly Thr Lys
1               5                   10

( 2 ) INFORMATION FOR SEQ ID NO:40:

( i ) SEQUENCE CHARACTERISTICS:
    ( A ) LENGTH: 70 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:40:

```
TCTCGATGAT  GTTGTTGATT  CTTCTAAATC  TTTTGTGATT  GAAAACTTTT  CTTCGTACCA        60
CGGGACTAAA                                                                    70
```

( 2 ) INFORMATION FOR SEQ ID NO:41:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:41:

```
TCTCGATGAT  GTTGTTGATT  CTTCTAAATC  TTTTGTGTTG  GAAAACTTTT  CTTCGTACCA        60
CGGGACTAAA                                                                    70
```

( 2 ) INFORMATION FOR SEQ ID NO:42:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:42:

```
ATGAAGCTTC  TCGATGATGT  TGTTGATTCT  TCTAAATCTT  TTGTGATGGA  AAACTTTTCT        60
TCGTACCACG  GGACTAAA                                                          78
```

( 2 ) INFORMATION FOR SEQ ID NO:43:

( i ) SEQUENCE CHARACTERISTICS:
        ( A ) LENGTH: 26 amino acids
        ( B ) TYPE: amino acid
        ( D ) TOPOLOGY: linear ( x i ) SEQUENCE DESCRIPTION: SEQ ID NO:43:

```
Met  Lys  Leu  Leu  Asp  Asp  Val  Val  Asp  Ser  Ser  Lys  Ser  Phe  Val  Met
  1              5                        10                       15
Glu  Asn  Phe  Ser  Ser  Tyr  His  Gly  Thr  Lys
                20                       25
```

( 2 ) INFORMATION FOR SEQ ID NO:44:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:44:

```
ATGGAGAAAA  AAATCACTGG  ATATACCACC  GTTGATATAT  C                             41
```

( 2 ) INFORMATION FOR SEQ ID NO:45:

( i ) SEQUENCE CHARACTERISTICS:
        ( A ) LENGTH: 17 amino acids
        ( B ) TYPE: amino acid
        ( D ) TOPOLOGY: linear ( x i ) SEQUENCE DESCRIPTION: SEQ ID NO:45:

Met Glu Lys Lys Ile Thr Asp Ser Leu Ala Val Val Leu Gln Arg Arg
1               5                   10                  15

Asp ( 2 ) INFORMATION FOR SEQ ID NO:46:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:46:

ATGGAGAAAA AAATTACGGA TTCACTGGCC GTCGTTTTAC AACGTCGTGA C        51

( 2 ) INFORMATION FOR SEQ ID NO:47:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:47:

ATGAAGCTAC TGTCTTCTAT CGAACAAGCA TGCGATATTT        40

( 2 ) INFORMATION FOR SEQ ID NO:48:

( i ) SEQUENCE CHARACTERISTICS:
        ( A ) LENGTH: 20 amino acids
        ( B ) TYPE: amino acid
        ( D ) TOPOLOGY: linear ( x i ) SEQUENCE DESCRIPTION: SEQ ID NO:48:

Met Lys Leu Leu Asp Asp Val Val Asp Ser Ser Lys Ser Phe Val Met
1               5                   10                  15

Glu Asn Phe Ser
            20

( 2 ) INFORMATION FOR SEQ ID NO:49:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:49:

ATGAAGCTTC TCGATGATGT TGTTGATTCT TCTAAATCTT TTGTGATGGA AAACTTTTCT        60

( 2 ) INFORMATION FOR SEQ ID NO:50:

( i ) SEQUENCE CHARACTERISTICS:
        ( A ) LENGTH: 72 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:50:

ATGGAGAAAA AAATCACTGG ATATACCACC GTTGATATAT CCCAATGGCA TCGTAAAGAA        60

CATTTTGAGG CA        72

( 2 ) INFORMATION FOR SEQ ID NO:51:

( i ) SEQUENCE CHARACTERISTICS:

( A ) LENGTH: 479 base pairs
( B ) TYPE: nucleic acid
( C ) STRANDEDNESS: both
( D ) TOPOLOGY: linear ( x i ) SEQUENCE DESCRIPTION: SEQ ID NO:51:

| | | | | | |
|---|---|---|---|---|---|
| AAGCTTCTTT | ACGATGCCAT | TGGGATATAT | CAACGGTGGT | ATAAAGCCGT | GGTTTTTAAA | 60
| AGTTATCAGG | CATGCACCTG | GTAGCTAGTC | TTTAAACCAA | TAGATTGCAT | CGGTTTAAAA | 120
| GGCAAGACCG | TCAAATTGCG | GGAAAGGGGT | CAACAGCCGT | TCAGTACCAA | GTCTCAGGGG | 180
| AAACTTTGAG | ATGGCCTTGC | AAAGGGTATG | GTAATAAGCT | GACGGACATG | GTCCTAACCA | 240
| CGCAGCCAAG | TCCTAAGTCA | ACAGATCTTC | TGTTGATATG | GATGCAGTAC | AGACTAAATG | 300
| TCGGTCGGGG | AAGATGTATT | CTTCTCATAA | CATATAGTCG | GACCTCTCCT | TAATGGGAGC | 360
| TAGCGGATGA | AGTGATGCAA | CACTGGAGCC | GCTGGGAACT | AATTTGTATG | CGAAAGTATA | 420
| TTGATTAGTT | TTGGAGTACT | CGTACGGATT | CACTGGCCGT | CCTGTTACAA | CGTCGTGAC | 479

( 2 ) INFORMATION FOR SEQ ID NO:52:

( i ) SEQUENCE CHARACTERISTICS:
( A ) LENGTH: 479 base pairs
( B ) TYPE: nucleic acid
( C ) STRANDEDNESS: both
( D ) TOPOLOGY: linear ( x i ) SEQUENCE DESCRIPTION: SEQ ID NO:52:

| | | | | | |
|---|---|---|---|---|---|
| AAGCTTCTTT | ACGATGCCAT | TGGGATATAT | CAACGGTGGT | ATAAAGCCGT | GGTTTTTAAA | 60
| AGTTATCAGG | CATGCACCTG | GTAGCTAGTC | TTTAAACCAA | TAGATTGCAT | CGGTTTAAAA | 120
| GGCAAGACCG | TCAAATTGCG | GGAAAGGGGT | CAACAGCCGT | TCAGTACCAA | GTCTCAGGGG | 180
| AAACTTTGAG | ATGGCCTTGC | AAAGGGTATG | GTAATAAGCT | GACGGACATG | GTCCTAACCA | 240
| CGCAGCCAAG | TCCTAAGTCA | ACAGATCTTC | TGTTGATATG | GATGCAGTAC | AGACTAAATG | 300
| TCGGTCGGGG | AAGATGTATT | CTTCTCATAA | CATATAGTCG | GACCTCTCCT | TAATGGGAGC | 360
| TAGCGGATGA | AGTGATGCAA | CACTGGAGCC | GCTGGGAACT | AATTTGTATG | CGAAAGTATA | 420
| TTGATTAGTT | TTGGAGTACT | CGTACGGATT | CACTGGCCGT | CCTGTTACAA | CGTCGTGAC | 479

( 2 ) INFORMATION FOR SEQ ID NO:53:

( i ) SEQUENCE CHARACTERISTICS:
( A ) LENGTH: 480 base pairs
( B ) TYPE: nucleic acid
( C ) STRANDEDNESS: both
( D ) TOPOLOGY: linear ( x i ) SEQUENCE DESCRIPTION: SEQ ID NO:53:

| | | | | | |
|---|---|---|---|---|---|
| AAGCTTCTTT | ACGATGCCAT | TGGGATATAT | CAACGGTGGT | ATAAAGCCGT | GGTTTTTAAA | 60
| AGTTATCAGG | CATGCACCTG | GTAGCTAGTC | TTTAAACCAA | TAGATTGCAT | CGGTTTAAAA | 120
| GGCAAGACCG | TCAAATTGCG | GGAAAGGGGT | CAACAGCCGT | TCAGTACCAA | GTCTCAGGGG | 180
| AAACTTTGAG | ATGGCCTTGC | AAAGGGTATG | GTAATAAGCT | GACGGACATG | GTCCTAACCA | 240
| CGCAGCCAAG | TCCTAAGTCA | ACAGATCTTC | TGTTGATATG | GATGCAGTAC | AGACTAAATG | 300
| TCGGTCGGGA | CCGTTGATAT | ATGGTTCATA | ACATATAGTC | GGACCTCTCC | TTAATGGGAG | 360
| CTAGCGGATG | AAGTGATGCA | ACACTGGAGC | CGCTGGGAAC | TAATTTGTAT | GCGAAAGTAT | 420
| ATTGATTAGT | TTTGGAGTAC | TCGTACGGAT | TCACTGGCCG | TCCTGTTACA | ACGTCGTGAC | 480

( 2 ) INFORMATION FOR SEQ ID NO:54:

( i ) SEQUENCE CHARACTERISTICS:
    ( A ) LENGTH: 487 base pairs
    ( B ) TYPE: nucleic acid
    ( C ) STRANDEDNESS: both
    ( D ) TOPOLOGY: linear ( x i ) SEQUENCE DESCRIPTION: SEQ ID NO:54:

| | | | | | | |
|---|---|---|---|---|---|---|
| AAGCTTCTTT | ACGATGCCAT | TGGGATATAT | CAACGGTGGT | ATAAAGCCGT | GGTTTTTAAA | 60 |
| AGTTATCAGG | CATGCACCTG | GTAGCTAGTC | TTTAAACCAA | TAGATTGCAT | CGGTTTAAAA | 120 |
| GGCAAGACCG | TCAAATTGCG | GGAAAGGGGT | CAACAGCCGT | TCAGTACCAA | GTCTCAGGGG | 180 |
| AAACTTTGAG | ATGGCCTTGC | AAAGGGTATG | GTAATAAGCT | GACGGACATG | GTCCTAACCA | 240 |
| CGCAGCCAAG | TCCTAAGTCA | ACAGATCTTC | TGTTGATATG | GATGCAGTAC | AGACTAAATG | 300 |
| TCGGTCGGGA | CCGTTGATAT | ATCCCAAACG | GTTCATAACA | TATAGTCGGA | CCTCTCCTTA | 360 |
| ATGGAGCTA | GCGGATGAAG | TGATGCAACA | CTGGAGCCGC | TGGGAACTAA | TTTGTATGCG | 420 |
| AAAGTATATT | GATTAGTTTT | GGAGTACTCG | TACGGATTCA | CTGGCCGTCC | TGTTACAACG | 480 |
| TCGTGAC | | | | | | 487 |

( 2 ) INFORMATION FOR SEQ ID NO:55:

( i ) SEQUENCE CHARACTERISTICS:
        ( A ) LENGTH: 1044 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:55:

| | | | | | | |
|---|---|---|---|---|---|---|
| GTCGACCTTT | TTAAGTCGGC | AAATATCGCA | TGTTTGTTCG | ATAGACATCG | AGTGGCTTCA | 60 |
| AAAGTTATCA | GGCATGCACC | TGGTAGCTAG | TCTTTAAACC | AATAGATTGC | ATCGGTTTAA | 120 |
| AAGGCAAGAC | CGTCAAATTG | CGGGAAAGGG | GTCAACAGCC | GTTCAGTACC | AAGTCTCAGG | 180 |
| GGAAACTTTG | AGATGGCCTT | GCAAAGGGTA | TGGTAATAAG | CTGACGGACA | TGGTCCTAAC | 240 |
| CACGCAGCCA | AGTCCTAAGT | CAACAGATCT | TCTGTTGATA | TGGATGCAGT | TCACAGACTA | 300 |
| AATGTCGGTC | GGGGAACAAC | ATGCGATATT | GTTCTCATAA | GATATAGTCG | GACCTCTCCT | 360 |
| TAATGGGAGC | TAGCGGATGA | AGTGATGCAA | CACTGGAGCC | GCTGGGAACT | AATTTGTATG | 420 |
| CGAAAGTATA | TTGATTAGTT | TTGGAGTACT | CGTCTCGATG | ATGTTGTTGA | TTCTTCTAAA | 480 |
| TCTTTTGTGA | TTGAAAACTT | TTCTTCGTAC | CACGGGACTA | AACCTGGTTA | TGTAGATTCC | 540 |
| ATTCAAAAAG | GTATACAAAA | GCCAAAATCT | GGTACACAAG | GAAATTATGA | CGATGATTGG | 600 |
| AAAGGGTTTT | ATAGTACCGA | CAATAAATAC | GACGCTGCGG | GATACTCTGT | AGATAATGAA | 660 |
| AACCCGCTCT | CTGGAAAAGC | TGGAGGCGTG | GTCAAAGTGA | CGTATCCAGG | ACTGACGAAG | 720 |
| GTTCTCGCAC | TAAAAGTGGA | TAATGCCGAA | ACTATTAAGA | AAGAGTTAGG | TTTAAGTCTC | 780 |
| ACTGAACCGT | TGATGGAGCA | AGTCGGAACG | GAAGAGTTTA | TCAAAAGGTT | CGGTGATGGT | 840 |
| GCTTCGCGTG | TAGTGCTCAG | CCTTCCCTTC | GCTGAGGGGA | GTTCTAGCGT | TGAATATATT | 900 |
| AATAACTGGG | AACAGGCGAA | AGCGTTAAGC | GTAGAACTTG | AGATTAATTT | TGAAACCCGT | 960 |
| GGAAAACGTG | GCCAAGATGC | GATGTATGAG | TATATGGCTC | AAGCCTGTGC | AGGAAATCGT | 1020 |
| GTCAGGCGAT | CTTTGTGACT | CGAG | | | | 1044 |

( 2 ) INFORMATION FOR SEQ ID NO:56:

( i ) SEQUENCE CHARACTERISTICS:
        ( A ) LENGTH: 1047 base pairs
        ( B ) TYPE: nucleic acid
        ( C ) STRANDEDNESS: both

-continued (D) TOPOLOGY: linear (xi) SEQUENCE DESCRIPTION: SEQ ID NO:56:

```
GTCGACCTTT  TTAAGTCGGC  AAATATCGCA  TGTTTGTTCG  ATAGACATCG  AGTGGCTTCA       60
AAAGTTATCA  GGCATGCACC  TGGTAGCTAG  TCTTTAAACC  AATAGATTGC  ATCGGTTTAA      120
AAGGCAAGAC  CGTCAAATTG  CGGGAAAGGG  GTCAACAGCC  GTTCAGTACC  AAGTCTCAGG      180
GGAAACTTTG  AGATGGCCTT  GCAAAGGGTA  TGGTAATAAG  CTGACGGACA  TGGTCCTAAC      240
CACGCAGCCA  AGTCCTAAGT  CAACAGATCT  TCTGTTGATA  TGGATGCAGT  TCACAGACTA      300
AATGTCGGTC  GGGCAAACAT  GCGATATTTG  CCGTTTGTCA  TAAGATATAG  TCGGACCTCT      360
CCTTAATGGG  AGCTAGCGGA  TGAAGTGATG  CAACACTGGA  GCCGCTGGGA  ACTAATTTGT      420
ATGCGAAAGT  ATATTGATTA  GTTTTGGAGT  ACTCGTCTCG  ATGATGTTGT  TGATTCTTCT      480
AAATCTTTTG  TGATTGAAAA  CTTTTCTTCG  TACCACGGGA  CTAAACCTGG  TTATGTAGAT      540
TCCATTCAAA  AAGGTATACA  AAAGCCAAAA  TCTGGTACAC  AAGGAAATTA  TGACGATGAT      600
TGGAAAGGGT  TTTATAGTAC  CGACAATAAA  TACGACGCTG  CGGGATACTC  TGTAGATAAT      660
GAAAACCCGC  TCTCTGGAAA  AGCTGGAGGC  GTGGTCAAAG  TGACGTATCC  AGGACTGACG      720
AAGGTTCTCG  CACTAAAAGT  GGATAATGCC  GAAACTATTA  AGAAAGAGTT  AGGTTTAAGT      780
CTCACTGAAC  CGTTGATGGA  GCAAGTCGGA  ACGGAAGAGT  TTATCAAAAG  GTTCGGTGAT      840
GGTGCTTCGC  GTGTAGTGCT  CAGCCTTCCC  TTCGCTGAGG  GGAGTTCTAG  CGTTGAATAT      900
ATTAATAACT  GGGAACAGGC  GAAAGCGTTA  AGCGTAGAAC  TTGAGATTAA  TTTTGAAACC      960
CGTGGAAAAC  GTGGCCAAGA  TGCGATGTAT  GAGTATATGG  CTCAAGCCTG  TGCAGGAAAT     1020
CGTGTCAGGC  GATCTTTGTG  ACTCGAG                                            1047
```

CELL ABLATION USING TRANS-SPLICING RIBOZYMES

This application is a division of application Ser. No. 08/090,193, now U.S. Pat. No. 5,641,673, which is the U.S. National Phase of PCT/US92/00277 (International filing date Jan. 16, 1992) (pending), which is a continuation-in-part of U.S. application Ser. No. 07/642,330, filed Jan. 17, 1991 (abandoned).

FIELD OF THE INVENTION

The present invention is directed to novel trans-splicing ribozymes and methods of cell ablation using these ribozymes.

BRIEF DESCRIPTION OF THE BACKGROUND ART

I. Group I Introns

RNA molecules with catalytic activity are called ribozymes or RNA enzymes (Cech, T. R., *Ann. Rev. Biochem.* 59:543–568 (1990). The *Tetrahymena thermophila* precursor rRNA contains an intron (a ribozyme) capable of catalyzing its own excision. This ribozyme is one of a class of structurally related Group I introns.

The splicing activity of the modified *T. thermophila* intron requires the presence of a guanosine cofactor and a divalent cation, either $Mg^{++}$ or $Mn^{++}$, and occurs via two sequential transesterification reactions (FIG. 1). First, a free guanosine is bound to the ribozyme and its 3' hydroxyl group is positioned to attack the phosphorus atom at the 5' splice site. The guanosine is covalently attached to the intron sequence and the 5' exon is released. Second, the phosphodiester bond located at the 3' splice site undergoes attack from the newly freed 3' hydroxyl group of the 5' exon, resulting in production of the ligated exon sequences. The excised intron subsequently undergoes a series of transesterification reactions, involving its 3' hydroxyl group and internal sequences, resulting in the formation of shortened circular forms.

These successive reactions are chemically similar and appear to occur at a single active site. The reactions of self-splicing are characterized by the formation of alternative RNA structures as differing RNA chains are each brought to form similar conformations around the highly conserved intron. Splicing requires the alignment of the intron-exon junctions across a complementary sequence termed the "internal guide sequence" or IGS.

The first cleavage at the 5' splice site requires the formation of a base-paired helix (P1) between the IGS and sequences adjacent the splice site. The presence of a U:G "wobble" base-pair within this helix defines the phosphodiester bond that will be broken in the catalytic reaction of the ribozyme. After cleavage of this bond, a portion of the P1 helix is displaced and a new helix, P10, is formed due to complementarity between the IGS and sequences adjacent the 3' splice site. An invariant guanosine residue precedes the phosphodiester at the 3' splice site, similar to the portion of the P1 sequence that it is displacing. Thus, ligation of the exons occurs in a reverse of the first cleavage reaction but where new exon sequences have been substituted for those of the intron. It may be noted that intron circularization reactions subsequent to exon ligation also involve base-pairing of 5' sequences across the IGS, and attack mediated by the 3' hydroxyl group of the intron's terminal guanine residue (Been, M. D. et al., "Selection Of Circularizaton Sites In A Group I IVS RNA Requires Multiple Alignments Of An Internal Template-Like Sequence," *Cell* 50:951 (1987)).

II. Catalytic Activities

In order to better define the structural and catalytic properties of the Group I introns, exon sequences have been stripped from the "core" of the *T. thermophila* intron. Cech, T. R. et al., WO 88/04300, describes at least three catalytic activities possessed by the Tetrahymena intron ribozyme: (1) a dephosphorylating activity, capable of removing the 3' terminal phosphate of RNA in a sequence-specific manner, (2) an RNA polymerase activity (nucleotidyl transferase), capable of catalyzing the conversion of oligoribonucleotides to polyribonucleotides, and (3) a sequence-specific endoribonuclease activity.

Isolated ribozyme activities can interact with substrate RNAs in trans, and these interactions characterized. For example, when truncated forms of the intron are incubated with sequences corresponding to the 5' splice junction, the site undergoes guanosien-dependent cleavage in mimicry of the first step in splicing. The substrate and endoribonucleolytic intron RNAs base-pair to form helix P1, and cleavage occurs after a U:G base-pair at the 4th–6th position. Phylogenetic comparisons and mutational analyses indicate that the nature of the sequences immediately adjacent the conserved uracil residue at the 5' splice site are unimportant for catalysis, provided the base-pairing of helix P1 is maintained (Doudna, J. A. et al., *Proc. Natl. Acad. Sci. USA* 86: 7402–7406 (1989)).

The sequence requirements for 3' splice-site selection appear to lie mainly within the structure of the intron itself, including helix P9.0 and the following guanosine residue which delineates the 3' intron boundary. However, flanking sequences within the 3' exon are required for the formation of helix P10 and efficient splicing, as shown by mutational analysis (Suh, E. R. et al., *Mol. Cell. Biol.* 10:2960–2965 (1990)). In addition, oligonucleotides have been ligated in trans, using a truncated form of the intron, and "external" guide sequence and oligonucleotides which had been extended by a 5' guanosine residue. The substrate oligonucleotides corresponding to 3' exon sequences were aligned solely by the formation of P10-like helices on an external template, prior to ligation (Doudna, J. A. et al., *Nature* 339:519–522 (1989)).

The cleavage activity of ribozymes has been targeted to specific RNAs by engineering a discrete "hybridization" region into the ribozyme, such hybridization region being capable of specifically hybridizing with the desired RNA. For example, Gerlach, W. L. et al., EP 321,201, constructed a ribozyme containing a sequence complementary to a target RNA. Increasing the length of this complementary sequence increased the affinity of this sequence for the target. However, the hybridizing and cleavage regions of this ribozyme were integral parts of each other. Upon hybridizing to the target RNA through the complementary regions, the catalytic region of the ribozyme cleaved the target. It was suggested that the ribozyme would be useful for the inactivation or cleavage of target RNA in vivo, such as for the treatment of human diseases characterized by the production of a foreign host's RNA. However, ribozyme-directed trans-splicing, (as opposed to trans-cleavage) was not described or suggested.

The endoribonuclease activities (the cleavage activities) of various naturally-occurring ribozymes have been extensively studied. Analysis of the structure and sequence of these ribozymes has indicated that certain nucleotides around the cleavage site are highly conserved but flanking sequences are not so conserved. This information has lead to the design of novel endoribonuclease activities not found in nature. For example, Cech and others have constructed novel ribozymes with altered substrate sequence specificity (Cech, T. R. et al., WO 88/04300; Koizumi, M. et al., *FEBS Lett.* 228:228–230 (1988); Koizumi, M. et al., *FEBS Lett.* 239:285–288 (1988); Haseloff, J. et al., *Nature* 334:585–591 (1987); and Heus, H. A. et al., *Nucl. Acids Res.* 18:1103–1108 (1990)). From early studies of the self-cleaving plant viroids and satellite RNAs (Buzayan, J. M. et al., *Proc. Natl. Acad. Sci. USA* 83:8859–8862 (1986), guidelines for the design of ribozymes that are capable of cleaving other RNA molecules in trans in a highly sequence specific have been developed (Haseloff, J. et al., *Nature* 334:585–591 (1988)). However, these constructs were unable to catalyze efficient, targeted trans-splicing reactions.

The joining of exons contained on separate RNAS, that is, trans-splicing, occurs in nature for both snRNP-mediated and self-catalyzed group I and group II introns. In trypanosome and *Caenorhabditis elegans* mRNAs, common 5' leader sequences are transcribed from separate genes and spliced to the 3' portions of the mRNAs (Agabian, N., *Cell* 61:1157–1160 (1990); Hirsh, D. et al., *Mol. Biol. Rep.* 14:115 (1990). These small "spliced leader" RNAs (slRNAs) consist of the 5' exon fused to sequences that can functionally substitute for U1 snRNA in mammalian snRNP-splicing extracts.

Also, both the group I and group II self-splicing introns are capable of exon ligation in trans in artificial systems (Been, M. D. et al., *Cell* 47:207–216 (1986); Galloway-Salvo, J. L. et al., *J. Mol. Biol.* 211:537–549 (1990); Jacquier, A. et al., *Science* 234:1099–1194 (1986); and Jarrell, K. A. et al., *Mol. Cell Biol.* 8:2361–2366 (1988)). Trans-splicing occurs in vivo for group II introns in split genes of chloroplasts (Kohchi, T. et al., *Nucl. Acids Res.* 16:10025–10036 (1988)), and has been shown for a group I intron in an artificially split gene in *Escherichia coli* (Galloway-Salvo, J. L. et al., *J. Mol. Biol.* 211:537–549 (1990)). In the latter case, a bacteriophage T4 thymidylate synthase gene (td) containing a group I intron was divided at the loop connecting the intron helix P6a. Transcripts of the td gene segments were shown to undergo trans-splicing in vitro, and to rescue dysfunctional *E. coli* host cells. Known base-pairings (P3, P6 and P6a) and possible tertiary interactions between the intron segments, allowed correct assembly and processing of the gene halves.

In vitro, the Tetrahymena ribozyme is capable of catalyzing the trans-splicing of single-stranded model oligoribonucleotide substrates. Four components were necessary: ribozyme, 3' single-stranded RNA, 5' exon and GTP. A shortened form of the Tetrahymena ribozyme (L-21 ScaI IVS RNA), starting at the internal guide sequence and terminating at $U_{409}$ has been used in such a reaction (Flanegan, J. B. et al., *J. Cell. Biochem.* (Supp.)12 part D:28 (1988)). Attack by GTP at the 5' splice site released the 5' exon which was then ligated by the ribozyme to the 3' exon in a transesterification reaction at the 3' splice site.

The in vivo use of ribozymes as an alternative to the use of antisense RNA for the targeting and destruction of specific RNAs has been proposed (Gerlach, W. L. et al., EP321,201; Cotten, M., *Trends Biotechnol.* 8:174–178 (1990); Cotten, M. et al., *EMBO J.* 8:3861–3866 (1989); Sarver, N. et al., *Science* 247:1222–1225 (1990)). For example, expression of a ribozyme with catalytic endonucleolytic activity towards an RNA expressed during HIV-1 infection has been suggested as a potential therapy against human immunodeficiency virus type 1 (HIV-1) infection (Sarver, N. et al., *Science* 247:1222–1225 (1990); Cooper, M., *CDC AIDS Weekly*, Apr. 3, 1989, page 2; Rossi, J. J., Abstract of Grant No. 1RO1AI29329 in Dialog's Federal Research in Progress File 265). However, such attempts have not yet been successful.

In a study designed to investigate the potential use of ribozymes as therapeutic agents in the treatment of human immunodeficiency virus type 1 (HIV-1) infection, ribozymes of the hammerhead motif (Hutchins, C. J. et al., *Nucl. Acids Res.* 14:3627 (1986); Keese, P. et al., in *Viroids and Viroid-Like Pathogens*, J. S. Semancik, ed., CRC Press, Boca Raton, Fla., 1987, pp. 1–47) were targeted to the HIV-1 gag transcripts. Expression of the gag-targeted ribozyme in human cell cultures resulted in a decrease (but not a complete disappearance of) the level of HIV-1 gag RNA and in antigen p24 levels (Sarver, N. et al., *Science* 247:1222–1225 (1990)). Thus, the medical effectiveness of Sarver's ribozyme was limited by its low efficiency since any of the pathogen's RNA that escapes remains a problem for the host.

Another problem with in vivo ribozyme applications is that a high ribozyme to substrate ratio is required for ribozyme inhibitory function in nuclear extracts and it has been difficult to achieve such ratios. Cotton et al. achieved a high ribozyme to substrate ration by microinjection of an expression cassette containing a ribozyme-producing gene operably linked to a strong tRNA promoter (a polymerase III promoter) in frog oocytes, together with substrate RNA that contains the cleavage sequence for the ribozyme (Cotton, M. et al., *EMBO J.* 8:3861–3866 (1989). However, microinjection is not an appropriate method of delivery in multicellular organisms.

The in vivo activity of ribozymes designed against mRNA coding for *Escherichia coli* β-galactosidase has been reported (Chuat, J.-C. et al., *Biochem. Biophys. Res. Commun.* 162:1025–1029 (1989)). However, this activity was only observed when the ribozyme and target were transfected into bacterial cells on the same molecule. Ribozyme activity was inefficient when targeted against an mRNA transcribed from a bacterial F episome that possessed the target part of the β-galactosidase gene.

Thus, current technological applications of ribozyme activities are limited to those which propose to utilize a ribozyme's cleavage activity to destroy the activity of a target RNA. Unfortunately, such applications often require complete destruction of all target RNA molecules, and/or relatively high ribozyme:substrate ratios to ensure effectiveness and this has been difficult to achieve. Most importantly, the modified ribozymes of the art are not capable of efficient, directed trans-splicing.

Accordingly, a need exists for the development of highly efficient ribozymes and ribozyme expression systems. Especially, the art does not describe an effective means in which to destroy an existing RNA sequence or to alter the coding sequence of an existing RNA by the trans-splicing of a new RNA sequence into a host's RNA.

SUMMARY OF THE INVENTION

Recognizing the potential for the design of novel ribozymes, and cognizant of the need for highly efficient methods to alter the genetic characteristics of higher eukaryotes in vivo, the inventors have investigated the use of ribozymes to alter the genetic information of native RNA's in vivo. These efforts have culminated in the development of highly effective trans-splicing ribozymes, and guidelines for the engineering thereof.

According to the invention, there is first provided an RNA or DNA molecule, such molecule encoding a trans-splicing ribozyme, such ribozyme being capable of efficiently splicing a new 3' exon sequence into any chosen target RNA sequence in a highly precise manner, in vitro or in vivo, and such molecule being novel in the ability to accomodate, any chosen target RNA or 3' exon sequences, and in the addition of a complementary sequence which enhances the specificity of such ribozyme.

According to the invention, there is also provided ribozyme, the molecule, such molecule encoding a ribozyme, the sequence for such ribozyme being a fusion RNA, such fusion RNA providing a first RNA sequence that is sufficient for targeting such ribozyme to hybridize to a target RNA, and further a second RNA sequence, such second RNA sequence capable of being transposed into the target RNA, and such second RNA sequence encoding an RNA sequence foreign to the targeted RNA sequence.

According to the invention, there is further provided an RNA or DNA molecule, such molecule encoding a ribozyme, the sequence for such ribozyme being a fusion RNA as described above, the first RNA sequence provided by the fusion RNA being a sequence for targeting such RNA molecule to hybridize to GAL4 RNA, and the second RNA sequence of the fusion RNA providing the coding sequence of the A chain of diphtheria toxin (DTA).

According to the invention, there is also provided an RNA or DNA molecule, such molecule encoding a conformationally disrupted ribozyme of the invention, a pro-ribozyme, such pro-ribozyme being substrate-activated, that is, such pro-ribozyme possessing neglible or no self-cleavage or trans-splicing activity, until being reactived by specific interaction with target RNA.

According to the invention, there is further provided an RNA or DNA molecule containing a ribozyme or pro-ribozyme expression cassette, such cassette being capable of being stably maintained in a host, or inserted into the genome of a host, and such cassette providing the sequence of a promoter capable of functioning in such host, operably linked to the sequence of a ribozyme or pro-ribozyme of the invention.

According to the invention, there is further provided an RNA or DNA molecule containing a ribozyme or pro-ribozyme expression cassette, such cassette being capable of being stably inserted into the genome of a host, such ribozyme expression cassette providing the sequence of a GAL4-responsive promoter operably linked to the sequence of a ribozyme or pro-ribozyme of the invention.

According to the invention, there is further provided a method for in-vitro trans-splicing, such method comprising the steps of (1) providing a ribozyme or pro-ribozyme of the invention and an appropriate substrate for such ribozyme in vitro, (2) further providing in vitro reaction conditions that promote the desired catalytic activity of such ribozyme or pro-ribozyme; and (3) allowing such ribozyme or pro-ribozyme to react with such substrate under such conditions.

According to the invention, there is further provided a method for in vivo trans-splicing, such method comprising the steps of (1) providing an RNA or DNA molecule of the invention to a host cell, (2) expressing the ribozyme or pro-ribozyme encoded by such molecule in such host cell, (3) expressing a substrate of such ribozyme or pro-ribozyme in such host cell, and (4) allowing such ribozyme or pro-ribozyme to react with such substrate in such host cell.

According to the invention, there is further provided a method for inactivating the activity of a target RNA, such method comprising (1) providing a ribozyme or pro-ribozyme of the invention, such ribozyme or pro-ribozyme being catalytically active against such target RNA, (2) providing such target RNA, and (3) providing conditions that allow such ribozyme or pro-ribozyme to express its catalytic activity towards such target RNA.

According to the invention, there is further provided a method for providing a desired genetic sequence to a host cell in vivo, such method comprising (1) providing a ribozyme or pro-ribozyme of the invention to a desired host cell, such ribozyme or pro-ribozyme being catalytically active against a target RNA in such host cell, (2) providing such ribozyme or pro-ribozyme encoding such desired genetic sequence, and (3) providing conditions that allow such ribozyme or pro-ribozyme to trans-splice such desired genetic sequence into the sequence of the target RNA.

According to the invention, there is further provided a method for cell ablation in multicellular plants and animals, such method comprising providing a ribozyme or pro-ribozyme of the invention to a any host cell, and especially into a fertilized embryonic host cell, such ribozyme or pro-ribozyme encoding the sequence of a gene toxic to such host cell and such ribozyme or pro-ribozyme being capable of trans-splicing with a desired target in such host cell.

According to the invention, there is further provided a method for engineering male or female sterility in agronomically important plant species, such method comprising the ablation of any cell necessary for fertility using a ribozyme or pro-ribozyme of the invention.

According to the invention, there is further provided a method of immunizing plants against plant pathogens, such method comprising the construction of transgenic plants capable of expressing a plant pathogen-specific fusion ribozyme or pro-ribozyme of the invention, and such ribozyme or pro-ribozyme being capable of ablating any host cell infected with such pathogen.

According to the invention, there is further provided a transformed, pathogen-resistant microorganism, such microorganism being resistant to a desired pathogen, such microorganism being transformed with a ribozyme or pro-ribozyme of the invention and such ribozyme or pro-ribozyme providing a catalytic activity that targets a nucleic acid molecule expressed by such pathogen.

According to the invention, there is further provided a viral pathogen capable of delivering a desired ribozyme or pro-ribozyme activity to a desired host, such ribozyme or pro-ribozyme activity being delivered by a ribozyme or pro-ribozyme of the invention.

DESCRIPTION OF THE FIGURES

FIG. 1 is a diagram of the mechanism of ribozyme splicing of the group I intron.

FIG. 2 is a diagram of structure of the design of ribozymes for trans-splicing.

FIG. 3A is a diagram of the design of a CAT-LacZ α-peptide trans-splicing ribozyme; FIG. 3B top structure depicts *Tetrahymena thermophila* self-splicing rRNA intron; bottom structure depicts CAT-LacZ trans-splicing ribozyme; is the complete DNA coding sequence of the CAT-LacZ ribozyme.

FIGS. 4A–4C present the sequences of cucumber mosaic virus (CMV) RNA 4 trans-splicing ribozymes. FIG. 4A depicts virus RNA target sequences; FIG. 4B depicts Oligonucleotide target sequences; FIG. 4C depicts CMV RNA4—diphtheria toxin A-chain trans-splicing ribozymes.

FIG. 5 is a comparison of cucumber mosaic virus 3/4 sequences.

FIG. 6A is a diagram of the design of a Gal4-Diphtheria toxin A (DTA) chain trans-splicing ribozyme; FIG. 6B: top structure depicts *Tetrahymena thermophila* self-splicing rRNA intron; bottom structure depicts Gal4-Dt-A trans-splicing ribozyme; is the complete coding sequence of the Gal4-DTA ribozyme with the isoleucine substitution.

FIGS. 13, and 13A–13C show the sequence and predicted secondary structure of the CAT-LacZ trans-splicing ribozyme. In FIG. 13C ribozyme "core" sequences are shaded (after Cech, *Gene* 73:259–271 (1988)). Helices P8 are shown for the unmodified ribozyme and pro-ribozymes 1 and 2, with 13 and 18 nucleotides, respectively, of sequence complementary to the "antisense" region (highlighted).

FIG. 14B, bottom, shows the active CAT-LacZ α-peptide trans-splicing pro-ribozyme, after base-pairing with the CAT mRNA, displacement of the helix P8—"antisense" pairing, and re-formation of helix P8.

FIG. 17 shows the "wild-type" and modified helices P8 used for pro-ribozyme design with possible base-pairs indicated in schematic form. Those bases which are complementary to the "anti-sense" portion of the corresponding pro-ribozyme, are shown in bold type. The number of complementary bases is listed next to each helix. The helices are ordered by the stability of the corresponding pro-ribozyme transcripts, as measured by the degree of "3' exon" hydrolysis during in vitro transcription.

DETAILED DESCRIPTION OF THE PREFERRED EMBODIMENTS

I. Definitions

Figure 2A:
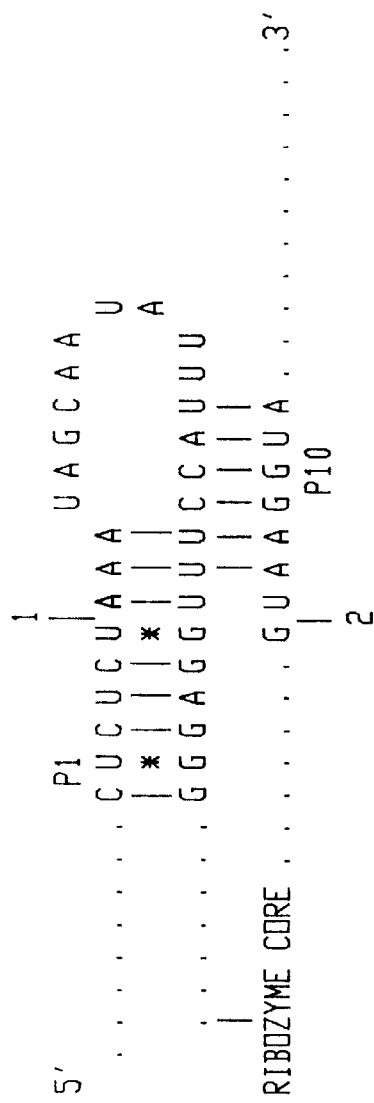
FIG. 2A depicts *Tetrahymena thermophila* self-splicing rRNA intron.

In the description that follows, a number of terms used in recombinant DNA (rDNA) technology are extensively utilized. In order to provide a clear and consistent understanding of the specification and claims, including the scope to be given such terms, the following definitions are provided.

Ribozyme. An RNA molecule that inherently possesses catalytic activity.

Trans-splice. A form of genetic manipulation whereby a nucleic acid sequence of a first polynucleotide is co-linearly linked to or inserted into the sequence of a second polynucleotide, in a manner that retains the 3'→5' phosphodiester linkage between such polynucleotides. By "directed" trans-splicing or "substrate-specific" trans-splicing is meant a trans-splicing reaction that requires a specific specie of RNA as a substrate for the trans-splicing reaction (that is, a specific specie of RNA in which to splice the transposed sequence). Directed trans-splicing may target more than one RNA specie if the ribozyme or pro-ribozyme is designed to be directed against a target sequence present in a related set of RNAs.

Target RNA. An RNA molecule that is a substrate for the catalytic activity of a ribozyme or pro-ribozyme of the invention.

Expression Cassette. A genetic sequence that provides sequences necessary for the expression of a ribozyme or pro-ribozyme of the invention.

Stably. By "stably" inserting a sequence into a genome is intended insertion in a manner that results in inheritance of such sequence in copies of such genome.

Operable linkage. An "operable linkage" is a linkage in which a sequence is connected to another sequence (or sequences) in such a way as to be capable of altering the functioning of the sequence (or sequences). For example, by operably linking a ribozyme or pro-ribozyme encoding sequence to a promoter, expression of the ribozyme or pro-ribozyme encoding sequence is placed under the influence or control of that promoter. Two nucleic acid sequences (such as a ribozyme or pro-ribozyme encoding sequence and a promoter region sequence at the 5' end of the encoding sequence) are said to be operably linked if induction of promoter function results in the transcription of the ribozyme or pro-ribozyme encoding sequence and if the nature of the linkage between the two sequences does not (1) result in the introduction of a frame-shift mutation, (2) interfere with the ability of the expression regulatory sequences to direct the expression of the ribozyme. Thus, a promoter region would be operably linked to a nucleic acid sequence if the promoter were capable of effecting the synthesis of that nucleic acid sequence.

II. Engineering of the Ribozyme of the Invention

The trans-splicing ribozymes, pro-ribozymes and methods of the invention provide, for the first time, a ribozyme capable of directed trans-splicing into any RNA sequence, and especially into mature (non-intron-containing) mRNA. The trans-splicing ribozyme as described herein, with its extended complementarity to the target, greatly differs from T. thermophila derived endoribonuclease activities described in the art. The additional complementarity of the ribozymes of the invention confers increased affinity and specificity for the target and the complementarity is not an integral part of the catalytic activity. In addition, cleavage occurs efficiently and precisely in the absence of denaturants and at high concentrations of Mg$^{++}$.

The guidelines described herein for the design of trans-splicing ribozymes are conservative, based on the well characterized properties of group I self-splicing introns and are meant to provide a general scheme for the design of any directed trans-splicing ribozyme. Accordingly, the guidelines presented herein are not limited to the group I intron of the T. thermophila pre-mRNA and may be used by one of skill in the art to design a ribozyme of the invention with other group I introns using such guidelines and knowledge in the art.

The native T. thermophila ribozyme (the intron sequence) is located from base 53 to base 465 in the sequence below of the T. thermophila extrachromosomal rDNA:

reaction (PCR) mutagenesis as described below, to produce a synthetic trans-splicing enzyme.

Substrate specificity of the ribozyme of the invention, that is, the ability of the ribozyme to "target" a specific RNA as a substrate, is conferred by fusing complementary sequences specific to the target (substrate) RNA to the 5' terminus of the ribozyme.

Directed trans-splicing specificity of the ribozyme of the invention, that is, specificity in trans-splicing a desired foreign sequence of interest with the sequence of a target RNA, is conferred by providing a new 3' exon at the 3' terminus of the ribozyme. Details of the design are further provided below.

To alter the structural and catalytic properties of the Group I introns, exon sequences replace the flanking sequence of such introns so that only the catalytic core of the intron, the ribozyme, remains. The resulting modified ribozyme can interact with substrate RNAs in trans. When truncated forms of the intron (i.e., the catalytic "core," i.e. truncated at the ScaI site, removing the last five nucleotides of the intron) are incubated with sequences corresponding to the 5' splice junction of the native ribozyme, the site undergoes guanosine-dependent cleavage in mimicry of the first step in splicing.

Engineering of the ribozymes of the invention requires consideration of the four guidelines that follow.

First, a splice site must be chosen within the target RNA. In the final trans-splicing complex, only the 5' portion of the P1 duplex is contributed by the target RNA. Only a single conserved residue, uracil, is required immediately 5' of the intended splice site. This is the sole sequence requirement in the target RNA. There is no inate structure required of the target RNA. Mature mRNA may be targeted and the trans-splicing reaction performed in the cell's cytoplasm rather than in the nucleus against pre-mRNA. This obviates the need for high concentrations of ribozyme in a cell's nucleus.

Second, having chosen a particular target sequence, compensating sequence changes must be added to the 5' section of the ribozyme in order to allow the formation of a suitable

| | | | | |
|---|---|---|---|---|
| TGACGCAATT | CAACCAAGCG | CGGGTAAACG | GCGGGAGTAA | CTATGACTCT |
| CTAAATAGCA | ATATTTACCT | TTGGAGGGAA | AAGTTATCAG | GCATGCACCT |
| CCTAGCTAGT | CTTTAAACCA | ATAGATTGCA | TCGGTTTAAA | AGGCAAGACC |
| GTCAAATTGC | GGGAAAGGGG | TCAACAGCCG | TTCAGTACCA | AGTCTCAGGG |
| GAAACTTTGA | CATGGCCTTG | CAAAGGGTAT | GGTAATAAGC | TGACGGACAT |
| GGTCCTAACC | ACGCAGCCAA | GTCCTAAGTC | AACAGATCTT | CTGTTGATAT |
| GGATGCAGTT | CACAGACTAA | ATGTCGGTCG | GGGAAGATGT | ATTCTTCTCA |
| TAAGATATAG | TCGGACCTCT | CCTTAATGGG | AGGTAGCGGA | TGAATGGATG |
| CAACACTGGA | GCCGCTGGGA | ACTAATTTGT | ATGCGAAAGT | ATATTGATTA |
| GTTTTGGAGT | ACTCGTAAGG | TAGCCAAATG | CCTCGTCATC | TAATTAGTGA |
| CGCGCATGAA | TGGATTA | [SEQ ID NO.1] | | |

(Kan, N. C. et al., *Nucl. Acids Res.* 10:2809–2822 (1982)).

As described herein, the directed trans-splicing ribozymes of the invention are engineered using the catalytic core of this intron. The intron, and its catalytic core can be isolated by methods known in the art. The catalytic core of the intron, that is, the truncated intron, differs form the full-length intron only in that it is truncated at the ScaI site, thus removing the last five nucleotides of the intron. The truncated intron RNA may be prepared by techniques known in the art or may be purchased commercially in kit form from commercial sources such as, for example, product #72000 from U.S. Biochemical, Cleveland, Ohio (RNAzyme™ Tet 1.0 Kit). This U.S. Biochemical kit provides ribozyme and the protocol for the use of the ribozyme. Transcribed Tet.1 cDNA may be used as the substrate for polymerase chain helix P1 between the target and ribozyme RNAs. It is highly desired is that the helix P1 should contain a U:G base-pair at the intended 5' splice site, and should be positioned at the 4th, 5th (preferred) or 6th position from the base of the helix (Doudna, J. A., et al., "RNA Structure, Not Sequence Determines The 5' Splice-Site Specificity of a Group I Intron," *Proc. Natl. Acad. Sci. USA* 86:7402–7406 (1989), incorporated herein by reference). For the native T. thermophila intron, P1 extends for an additional 3 base pairs past the intended 5' splice site, and, in a preferred embodiment, this is maintained in the trans-splicing ribozyme of the invention. For trans-splicing to be efficient, the substrate and endoribonucleolytic intron RNAs must base-pair to form helix P1, with a resulting wobble U:G base-pair. Cleavage of the target RNA occurs at the phosphodiester bond immediately 3' to (after the) U:G base-pair. Phylogenetic comparisons and mutational analyses indicate that the nature of the sequences immediately adjacent the conserved uracil residue at the 5' splice site are unimportant for catalysis, provided the base-pairing of helix P1 is maintained.

shown herein, an arbitrary length of around 40 residues has been used. Other lengths may be used provided they are not detrimental to the desired effect.

For example, starting with the *T. thermophila* self-splicing intron (diagrammed below):

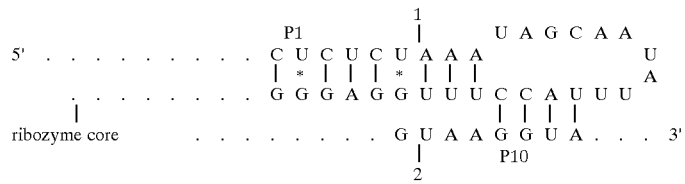

Figure 2B:
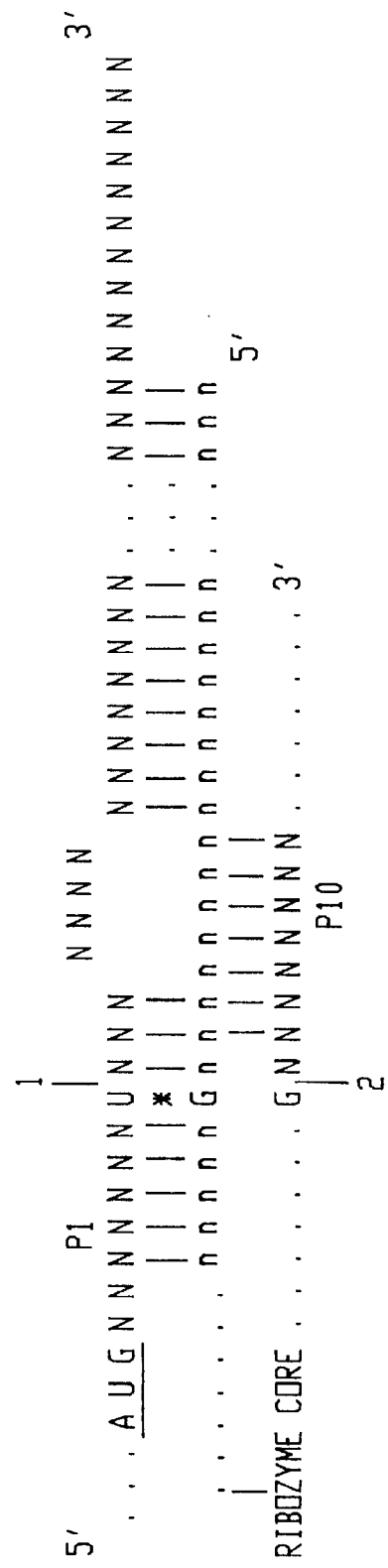
FIG. 2B depicts Target mRNA and trans-splicing ribozyme or pro-ribozyme of the invention.

Third, the exon sequences flanking the 3' splice site must be chosen, and adjustments made in the 5' section of the ribozyme, if necessary, to allow the formation of a stable P10 helix. While the P10 helix may be dispensesd with if necessary, its presence enhances splicing and preferred embodiments of the ribozyme of the invention retain the P10 helix (Suh, E. R. et al., "Base Pairing Between The 3' Exon And An Internal Guide Sequence Increases 3' Splice Site Specificity in the Tetrahymena Self-Splicing rRNA Intron," *Mol. Cell. Biol.* 10:2960–2965 (1990)). The helices P1 and P10 overlap along the *T. thermophila* intron IGS, and the 2nd and 3rd residues following both the 5' and 3' splice sites are complementary to the same residues in the IGS (FIG. 2). While there may be some advantage in following this, many natural group I introns do not share this constraint, so the choice of 3' exon sequences may be determined primarily by experimental considerations. Such considerations reflect the wide flexibility in choice of splice sites. For example, if it is desired to join two sequences at a given point, the sequence at such point cannot be mutated or otherwise altered by the trans-splicing event. Either P1 or P10 can be made shorter if the overlapping sequences don't otherwise accomodate for the desired splice site.

The sequence requirements for 3' splice-site selection appear to lie mainly within the structure of the intron (the ribozyme) itself, including helix P9.0 and the adjoining 3' guanosine residue which delineates the 3' intron boundary. P9.0 is wholly contained within the intron sequences and helps define the adjacent 3' splice site. For the trans-splicing design, the P9.0 helix and the rest of the functional RNA elements within the intron are not altered. The structural characteristics of the P9.0 helix are known (Michel, F. et al., "The Guanosine Binding Site of the Tetrahymena Ribozyme," *Nature* 342:391–395 (1989)). However, flanking sequences within the 3' exon are required for the formation of helix P10 and efficient splicing, as shown by mutational analysis.

Fourth, a region of complementary sequence is placed at the 5' terminus of the trans-splicing ribozyme in order to increase its affinity and specificity for the target RNA. As (The "1" and "2" in the above diagram (and in other ribozyme diagrams throughout the application) note the first and second splice sites, respectively.)

(1) a "5'" site is chosen adjacent to a uracil residue within a chosen target RNA. The sequences involved in complementarity do not immediately abut sequences involved in P1 helix formation but are separated, for example, by five nucleotides also involved in P10 formation;

(2) sequences complementary to the chosen RNA are fused to the 5' portion of the self-splicing Group I intron. Base-pairing between ribozyme and target RNA allow formation the of the helix P1;

(3) the chosen "3' exon" sequences are fused to the 3' portion of the ribozyme, maintaining the conserved helix P10; and (4) to increase affinity for the target RNA, if desired, a section of extended sequence complementarity is fused to the 5' portion of the ribozyme to allow the formation of 30–40 base-pairs.

The alignment of the resulting trans-splicing ribozyme with its target RNA may be diagrammed as shown immediately below. The target RNA sequence represents the top line. The ribozyme sequence is aligned below it, a continuous sequence wrapping around the lower two lines wherein the hybridization of the nucleotides at the 5' and 3' ends and P1 and P10 of the ribozyme may be seen.

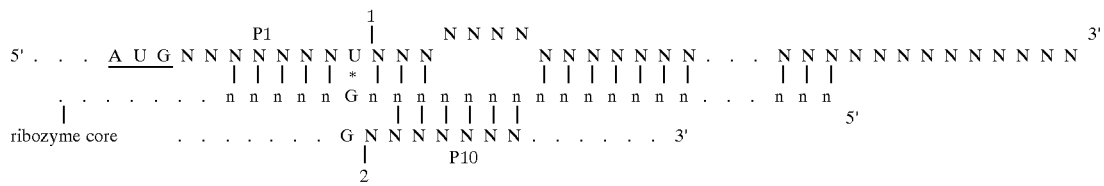

Alignment of the Ribozyme of the Invention with a Target RNA

According to the invention, trans-splicing ribozymes can be designed that will trans-splice essentially any RNA sequence onto any RNA target. It is not necessary that the target contain an intron sequence or that the ribozyme be an intron in the target sequence. For example, a strategy for such design may include (1) the identification of the desired target RNA (2) cloning and/or sequencing of the desired target RNA or portion thereof (3) selection of a desired coding sequence to trans-splice into the target RNA, (4) the construction of a ribozyme of the invention capable of hybridizing to such target using the guidelines herein and (5) confirmation that the ribozyme of the invention will utilize the target as a substrate for the specific trans-splicing reaction that is desired and (6) the insertion of the ribozyme into the desired host cell.

Choice of a target RNA will reflect the desired purpose of the trans-splicing reaction. If the purpose of the reaction is to inactivate a specific RNA, then such RNA must be trans-spliced at a position that destroys all functional peptide domains encoded by such RNA and at a position that does not result in continued expression of the undesired genetic sequences. If more than one allele of the gene encoding such RNA exists, the ribozyme should preferably be designed to inactivate the target RNA at a site common to all expressed forms. Alternatively, more than one ribozyme may be provided to the cell, each designed to inactivate a specific allelic form of the target RNA.

When only inactivation of the target RNA is desired, and not the expression of a new, desired RNA sequence, it is not necessary that the foreign RNA donated by the ribozyme provide a sequence capable of being translated by the host cell, and a sequence containing translational stop codons may be used as a truncated intron, for example, the intron ribozyme truncated at the ScaI site.

If the purpose of the trans-splicing reaction is to provide a genetic trait to a host cell, then the choice of target RNA will reflect the desired expression pattern of the genetic trait. If it is desired that the genetic trait be continuously expressed by the host, then the target RNA should also to be continuously expressed. If it is desired that the genetic trait be selectively expressed only under a desired growth, hormonal, or environmental condition, then the target RNA should also be selectively expressed under such conditions.

It is not necessary that expression of the ribozyme itself be selectively limited to a desired growth, hormonal, or environmental condition if the substrate for such ribozyme is not otherwise present in the host as the ribozyme itself is not translated by the host. Thus, sequences encoded by the RNA donated by the ribozyme of the invention are not translated in a host until the trans-splicing event occurs and such event may be controlled by the expression of the ribozyme substrate in the host.

If desired, expression of the ribozyme may be engineered to occur in response to the same factors that induce expression of a regulated target, or, expression of the ribozyme may be engineered to provide an additional level of regulation so as to limit the occurrence of the trans-splicing event to those conditions under which both the ribozyme and target are selectively induced in the cell, but by different factors, the combination of those factors being the undesired event. Such regulation would allow the host cell to express the ribozyme's target under those conditions in which the ribozyme itself was not co-expressed.

The sequence of the ribozyme domain that hybridizes to the target RNA is determined by the sequence of the target RNA. The sequence of the target RNA is determined after cloning sequences encoding such RNA or after sequencing a peptide encoded by such target and deducing an RNA sequence that would encode such a peptide. Cloning techniques known in the art may be used for the cloning of a sequence encoding a target RNA.

The selection of a desired sequence to be trans-spliced into the target RNA (herein termed the "trans-spliced sequence") will reflect the purpose of the trans-splicing. If a trans-splicing event is desired that does not result in the expression of a new genetic sequence, then the trans-spliced sequence need not encode a translatable protein sequence. If a trans-splicing event is desired that does result in the expression of a new genetic sequence, and especially a new peptide or protein sequence, then the trans-spliced sequence may further provide translational stop codons, and other information necessary for the correct translational processing of the RNA in the host cell. If a specific protein product is desired as a result of the trans-splicing event then it would be necessary to maintain the amino acid reading frame in the resulting fusion.

The identification and confirmation of the specificity of a ribozyme of the invention is made by testing a putative ribozyme's ability to catalyze the desired trans-splicing reaction only in the presence of the desired target sequence. The trans-splicing reaction should not occur if the only RNA sequences present are non-target sequences to which such ribozyme should not be responsive (or less responsive). Such characterization may be performed with the assistance of a marker such that correct (or incorrect) ribozyme activity may be more easily monitored. In most cases it is sufficient to test the ribozyme against its intended target in vitro and then transform a host cell with it for study of its in vivo effects.

When it is desired to eliminate a host's RNA, such elimination should be as complete as possible. When it is desired to provide a new genetic sequence to a host cell, the trans-splicing reaction of the invention need not be complete. It is an advantage of the invention that, depending upon the biological activity of the peptide that is translated from such genetic sequence, the trans-splicing event may in fact be quite inefficient, as long as sufficient trans-splicing occurs to provide sufficient mRNA and thus encoded polypeptide to the host for the desired purpose.

Transcription of the ribozyme of the invention in a host cell occurs after introduction of the ribozyme gene into the host cell. If the stable retention of the ribozyme by the host cell is not desired, such ribozyme may be chemically or enzymatically synthesized and provided to the host cell by mechanical methods, such as microinjection, liposome-mediated transfection, electroporation, or calcium phosphate precipitation. Alternatively, when stable retention of the gene encoding the ribozyme is desired, such retention may be achieved by stably inserting at least one DNA copy of the ribozyme into the host's chromosome, or by providing a DNA copy of the ribozyme on a plasmid that is stably retained by the host cell.

Preferably the ribozyme of the invention is inserted into the host's chromosome as part of an expression cassette, such cassette providing transcriptional regulatory elements that will control the transcription of the ribozyme in the host cell. Such elements may include, but not necessarily be limited to, a promoter element, an enhancer or UAS element, and a transcriptional terminator signal. Polyadenylation is not necessary as the ribozyme is not translated. However, such polyadenylation signals may be provided in connection with the sequence encoding the element to be trans-spliced.

Expression of a ribozyme whose coding sequence has been stably inserted into a host's chromosome is controlled by the promoter sequence that is operably linked to the ribozyme coding sequences. The promoter that directs expression of the ribozyme may be any promoter functional in the host cell, prokaryotic promoters being desired in prokaryotic cells and eukaryotic promoters in eukaryotic cells. A promoter is composed of discrete modules that direct the transcriptional activation and/or repression of the promoter in the host cell. Such modules may be mixed and matched in the ribozyme's promoter so as to provide for the proper expression of the ribozyme in the host. A eukaryotic promoter may be any promoter functional in eukaryotic cells, and especially may be any of an RNA polymerase I, II or III specificity. If it is desired to express the ribozyme in a wide variety of eukaryotic host cells, a promoter functional in most eukaryotic host cells should be selected, such as a rRNA or a tRNA promoter, or the promoter for a widely expressed mRNA such as the promoter for an actin gene, or a glycolytic gene. If it is desired to express the ribozyme only in a certain cell or tissue type, a cell-specific (or tissue-specific) promoter elements functional only in that cell or tissue type should be selected.

The trans-splicing reaction is chemically the same whether it is performed in vitro or in vivo. However, in vivo, since cofactors are usually already present in the host cell, the presence of the target and the ribozyme will suffice to result in trans-splicing.

The trans-splicing ribozymes and methods of the invention are usful in producing a gene activity useful for the genetic modification, and/or cell death, of targeted cells. For example, the trans-splicing reaction of the invention is useful to introduce a protein with toxic properties into a desired cell. The susceptibility of cells will be determined by the choice of the target RNA and the regulatory controls that dictate expression of the ribozyme. For example, a ribozyme that transposes an RNA sequence encoding a toxic protein may be engineered so that expression of the ribozyme will depend upon the characteristics of an operably-linked promoter. In a highly preferred embodiment, diptheria toxin peptide A is encoded by that part of the ribozyme that is transposed into a desired target in the host. Conditional expression of the ribozyme and diphtheria toxin peptide A chain results in the death of the host cell. Other useful peptide toxins include ricin, exotonin A, and herpes thymidine kinase (Evans, G. A., *Genes & Dev.* 3:259–263 (1989)). In addition, various lytic enzymes have the potential for disrupting cellular metabolism. For example, a fungal ribonuclease may be used to cause male sterility in plants (Mariani, C. et al., *Nature* 347:737–741 (1990)). Particular tissues might be destroyed due to limited expression of the target RNA. Further, if a viral RNA is used as target, new forms of virus resistance, or therapies may be engineered.

A binary system for control of tissue-specific gene expression and/or for ectopic ablation may be designed using the ribozymes of the invention. For example, lines of Drosophila that express the yeast transcription activator GAL4 in a tissue and spatial-specific pattern using P-element enhancer-trap vectors may be used. Any transcriptional activator may be used in place of GAL4 and the invention is not intended to be limited to GAL4. A gene encoding a fusion ribozyme that is capable of trans-splicing the DTA sequence may be placed under the control of the GAL4-UAS promoter and inserted into Drosophila in a genetically stable manner. Such ribozymes will not be expressed in Drosophila in the absence of GAL4. Accordingly, crossing Drosophila hosts genetically carrying this ribozyme construct with Drosophila hosts that express GAL4 in a tissue-specific manner result in progeny that, when GAL4 expression is induced, exhibit a pattern of cell death similar to the pattern of GAL4 expression.

In addition, by targetting the ribozyme to trans-splice with the GAL4 mRNA, the splicing activity of the ribozyme inactivates GAL4 expression and ribozyme expression may be self-regulated.

Pro-ribozymes

A trans-splicing ribozyme, as described above, consists of three fused sequence elements—a 5' "anti-sense" region which is complementary to the target RNA, the catalytic region which is based on a self-splicing Group I intron, and 3' "exon" sequences. The 5' region can base pair with the chosen target RNA, to bring it into proximity with the catalytic sequences of the Group I intron. The structure of the Group I intron provides a chemical environment suitable to catalyze the precise splicing of the target RNA with the 3' "exon" sequences. However, in the absence of the appropriate target RNA, the ribozyme sequences can still catalyze scission at the 3' "exon" junction (similar hydrolysis is seen for Group I self-splicing intons (Zaug et al., *Science* 231:470–475 (1986)), and may be able to catalyze illegitimate splicing events through transient base-pairing of the ribozyme with heterologous RNA sequences (which may include their own). Such side-reactions and illegitimate splicing events are unwanted, and may be deleterious. For example, if trans-splicing is to be used for conditional delivery of a toxin in vivo, illegitimate trans-splicing might result in unexpected expression of the toxic activity. Spontaneous cleavage at the 3' "exon" junction would lower the efficiency of trans-splicing.

To help avoid these problems, "pro-ribozyme" forms of the trans-splicing RNAs have been constructed wherein for example, helix P8 is disrupted. The pro-ribozymes are constructed to contain extra self-complementary sequences which cause the catalytic center of the ribozyme to be mis-folded. The pro-ribozymes are inactive in the absence of the intended target RNA; active forms are only formed after base-pairing of the ribozyme and target RNAs—with consequent displacement of the interfering secondary structure within the ribozyme. Pro-ribozymes are intended to be catalytically inert species in the absence of the target RNA, to eliminate unwanted self-cleavage, self-splicing and illegitimate trans-splicing reactions in vitro and in vivo (FIG. 12).

The pro-ribozymes described here are conformationally disrupted and therefore inactive forms of the trans-splicing activities. Thus the pro-ribozymes possess little self-cleavage activity. They are only re-activated by specific interaction with the target RNA, and thus are substrate-activated ribozymes which are less likely to catalyze trans-splicing to an unintended target RNA. Trans-splicing ribozymes are intended to be used for the delivery of new gene activities in vivo, and any reduction in the extent of unwanted side reactions or illegitimate splicing is desirable, and may be necessary.

While the disruption of helix P8 has been exemplified here for the trans-splicing pro-ribozymes, other helices which are required for catalytic activity could also have been used.

The same approach, of disrupting the conformation of a catalytically important structure in such a way that only base-pairing with the intended substrate RNA will allow the formation of an active ribozyme, could be applied to other ribozyme designs. For example, the loop sequence of a "hammerhead" type endoribonuclease (Haseloff et al., *Nature* 334:585–591 (1988)) could be extended and made complementary to one of the "anti-sense" arms of the ribozyme—similar to the above modification of helix P8. Endoribonuclease activity would only be exhibited after base-pairing with the chosen target RNA, displacement of the disrupting secondary structure, and reformation of the stem-loop structure required for catalysis. This would effectively increase the specificity of the ribozyme of its target.

In addition, the activation of a pro-ribozyme need not rely on base-pairing with the substrate itself. Instead, a chosen third RNA or ssDNA or even protein might be required for activity. An additional base-pairing or RNA-protein interaction would be required for the formation of an active ribozyme complex. The availability of such additional components would determine ribozyme activity, and could be used to alter ribozyme selectivity.

The ribozyme or pro-ribozyme of the invention may be introduced into any host cell, prokaryotic or eukaryotic and especially into a plant or mammalian host cell, and especially a human cell, either in culture or in vivo, using techniques known in the art appropriate to such hosts. The ribozymes of the invention may also be engineered to destroy viruses. In one embodiment, the ribozyme or pro-ribozyme of the invention is provided in a genetically stable manner to a host cell prior to a viral attack. Infection by the appropriate virus, or expression of the latent virus in such host cell, (resulting in the appearance of the ribozyme's or pro-ribozyme target RNA in the host cell), would stimulate the catalytic activity of the ribozyme and destruction of the viral RNA target and/or production of a toxin via trans-splicing resulting in death of the virus infected cells. In another embodiment, the ribozyme or pro-ribozyme may be engineered and packaged into the virus itself. Such embodiments would be especially useful in the design of viruses for investigative purposes, wherein the ribozyme or pro-ribozyme may be designed to destroy the function of a specific viral RNA and thus allow the study of viral function in the absence of such RNA. Viruses carrying ribozymes may also be used as carriers to transfect host cells with a desired ribozyme or pro-ribozyme activity.

Male or female sterility may be engineered in agronomically important species using the ribozymes or pro-ribozymes of the invention. For example, male sterility in tobacco may be engineered by targetting TA29 or TA13 mRNA (tobacco anther-specific genes; Seurinck, J. et al., *Nucl. Acids Res.* 18:3403 (1990) with a ribozyme or pro-ribozyme of the invention that trans-splices the DTA 3' exon into those targets.

The form of crop plants may be manipulated by selective destruction or modification of tissues using the ribozymes or pro-ribozymes of the invention. For example, seedless fruits may be made by targetting the seed storage protein mRNA with a ribozyme or pro-ribozyme of the invention that trans-splices the DTA 3' exon into the target.

Transgenic plants may be protected against infection by expression of virus-specific ribozymes or pro-ribozyme to kill infected cells. This would be an artificial form the "hypersensitive response." For example, cucumber mosaic virus coat protein mRNA may be targeted with a ribozyme or pro-ribozyme of the invention that trans-splices the DTA 3' exon into the target.

Populations of micro-organisms may be made resistant to specific pathogens by introduction of trans-splicing ribozymes or pro-ribozymes. For example, cheese-making bacteria may be made resistant to phage infection by targetting the phage RNA with a bacterial toxin gene or lytic enzyme encoded by the 3' exon provided by the ribozyme or pro-ribozyme of the invention, for example, which would interfere with phage replication by causing premature lysis after phage infection.

Virus pathogens could be constructed to deliver toxic activities via trans-splicing. In this way, specific cell types could be targeted for ablation, such as for cancer or viral therapy. For example, HIV mRNA may be targeted by a ribozyme or pro-ribozyme of the invention that carries the DTA 3' exon, for either virus or liposome delivery.

The examples below are for illustrative purposes only and are not deemed to limit the scope of the invention.

EXAMPLES

Example 1

Construction and Characterization of a CAT-LacZ Trans-Splicing Ribozyme

I. PCR Amplification and Cloning of the Ribozyme of the Invention

Following the guidelines outlined above, a trans-splicing fusion ribozyme was designed that will splice a portion of the amino-terminal coding sequence of *E. coli* β-galactosidase (LacZ) mRNA to a site in the chloramphenicol acetyl transferase (CAT) mRNA (FIG. 3). The sections of new sequence flanking the *T. thermophila* ribozyme core and the 3' exon were synthesized as oligonucleotides. The intact ribozyme sequence was then assembled by successive polymerase chain reactions, using the synthetic adaptor oligonucleotides as primers with ribozyme and β-galactosidase DNA templates (while there are other methods available, this method is most convenient).

For the construction of a ribozyme capable of splicing β-galactosidase (LacZ) α-peptide coding sequence to a site in the 5' coding sequence of the chloramphenicol acetyl transferase (CAT), three oligonucleotides were synthesized. Oligonucleotide 1

5'-GGCCA AGCTT CTTTA CGATG CCATT GGGAT ATATC AACGG TGGTA TAAAC CCGTG GTTTT TAAAA GTTAT CAGGC ATGCA CC-3' [SEQ ID NO. 2]
Oligonucleotide 2

5'-GATTA GTTTT GGAGT ACTCG TACGG ATTCA CGGCC GTCGT TTTAC AA-3' [SEQ ID NO. 3]
Oligonucleotide 3

5'-GGCCG AATTC TTACA ATTTC CATTC AGGCT GCGCA ACTGT TGG-3' [SEQ ID NO. 4]
Oligonucleotides 2 and 3 (200 pmoles each) were combined with 0.1 μg PvuII-cut pGEM4 DNA (which contained the LacZ α-peptide sequence), and subjected to PCR amplification in a volume of 100 μl containing:

50 mM KCl, 10 mM Tris-HCl pH 8.3, 1.5 mM $MgCl_2$, 0.4 mM dNTPs, 0.1% gelatin, and 5 U TaqI DNA polymerase,
and incubated for 30 cycles, 1 min @ 94° C., 2 mins @ 50° C., 2 mins @ 72° C.

Plasmid pGEM4 is commercially available from Promega Corporation, Madison Wis., U.S.A.

The amplified product of 210 base-pairs was purified using low-gelling temperature agarose electrophoresis, and was used as primer in a second round of PCR amplification.

Following the second round of PCR amplification, 2.0 μg of 210 base-pair amplified product, 200 pmoles oligonucleotide 1 and 0.1 μg 450 base-pair fragment containing the *T. thermophila* IVS were mixed and subjected to PCR amplification using the conditions shown above. The resulting 660 base-pair product was digested with the restriction endonucleases EcoRI and HindIII, and cloned into the plasmid vector pGEM4. The complete sequence of the CAT-LacZ α-peptide ribozyme DNA sequence is presented as SEQ ID NO. 5 and FIG. 3B.

The cloning vector containing the cloned sequences was transformed into, and propagated in, the bacterial host XL1/Blue (Strategene, La Jolla, Calif.), using techniques known in the art (Maniatis, *Molecular Cloning, A Laboratory Guide,* 2nd edition, 1989, Cold Spring Harbor Laboratory, Publishers). However, any bacterial host capable of stably maintaining the vector may be used, for example the JM109.

The plasmid may be extracted from the host cell for further analysis using techniques commonly known in the art (Maniatis, *Molecular Cloning, A Laboratory Guide,* 2nd edition, 1989, Cold Spring Harbor Laboratory, Publishers).

II. In vitro Transcription of Cloned Ribozyme and Target RNAs

Using standard procedures, cloned sequences were purified from the bacterial host and the plasmid linearized using a restriction endonuclease that does not cut the ribozyme sequence, (for example, EcoRI), and transcribed using T7 RNA polymerase in a volume of 100 $\mu$l, containing:

5 $\mu$g linearized plasmid DNA, 40 mM Tris-HC pH 7.5, 6 mM $MgCl_2$, 2 mM spermidine, 10 mM NaCl, 10 mM DTT, 1 mM NTPs (containing 20 $\mu$Ci [$\alpha$-$^{32}$P]UTP, if labelled RNA transcripts were desired), 100 U RNasin, and 50 U T7 RNA polymerase, and the reaction was incubated at 37° C. for 2 hours.

RNA transcripts were purified by 5% polyacrylamide gel electrophoresis before use (TBE, 7M urea gel). RNAs containing active *T. thermophila* IVA sequences undergo some spontaneous scission at the 3' intron-exon junction during transcription. Fragments are removed by electrophoretic purification for clarity of analysis during subsequent trans-splicing assays.

III. In Vitro Trans-splicing Reaction Conditions

Target and/or trans-splicing ribozymes are incubated under the following conditions:

0.1–0.5 $\mu$g RNA component (amount depends on type of experiment, usually ribozyme in 5-fold excess of target), 30 mM Tris-HCl pH 7.5, 100 mM NaCl, 2mM GTP, 5 mM $MgCl_2$, in a volume of 5 $\mu$l at 42° C., 60 mins.

The reaction is diluted with 95 $\mu$l 0.1 mM $Na_2EDTA$, 200 mM NaCl, and ethanol precipated. The RNAs are then analysed on 5% polyacrylamide gels containing TBE buffer, 7M urea and 25% formamide, and autoradiographed.

IV. Assay of Endonucleolytic Activity

After base-pairing of the ribozyme and target, the first step in trans-splicing is the guanosine mediated cleavage of the target RNA at the intended 5' splice site. Annealing and trans-splicing may be performed in a buffer such as 30 mM Tris-HCl, pH 7.5, 100 mM NaCl, 5 mM $MgCl_2$, 2 mM GTP at 42° C. As the 3' splice site is dispensable for this reaction, truncated trans-splicing ribozymes should behave as highly-specific endoribonucleases. To test this activity, shortened in vitro transcripts of the CAT-LacZ $\alpha$-peptide trans-splicing ribozyme described above (SEQ ID NO. 5 and FIG. 3) were incubated with CAT mRNA sequences. The CAT-LacZ ribozyme cassette is on a HindIII-EcoRI fragment. The ScaI cleavage site marks a position 5 bases upstream of the 3' splice site. The ribozyme specifically cleaved the target RNA at the expected single site to produce the expected size fragments.

V. The Trans-splicing Reaction

To confirm the ability of the CAT-LacZ $\alpha$-peptide ribozyme to catalyze the ligation of 3' exon sequences at the 5' splice site, various forms were incubated with radiolabelled CAT RNA. Ribozyme transcripts were synthesized from DNA templates which had been 3' truncated at one of several positions, ranging from the end of the ribozyme core through the exon sequence. Incubation with labelled CAT led to the formation of the expected spliced products, which differed in length depending on the extent of 3' exon sequence.

In addition, a certain proportion of the CAT-LacZ $\alpha$peptide ribozyme molecules underwent spontaneous cleavage at the 3' splice site during in vitro transcription, similar to the intact *T. thermophila* intron. These cleaved forms, terminated at the guanosine residue adjacent the 3' splice site, were also incubated with CAT RNA. In this case, the ribozyme itself is ligated to a 3' portion of the CAT RNA, to produce a product of about 550 nucleotides in size. This reaction is similar to the self-circularization of the intact intron, and the same ligation product is found in the other trans-splicing reactions.

VI. Accuracy of the Trans-splicing

The products from a CAT-LacZ $\alpha$-peptide trans-splicing reaction were reverse-transcribed, and amplified by polymerase chain reaction using two oligonucleotides complementary to sequences on either side of the predicted splice sites. Amplified sequences were cloned and sequenced. Individual recombinants showed no variation from the expected sequence of the spliced products. As found in studies with the intact intron, splicing appears to be highly accurate.

Accordingly, the studies above show that a trans-splicing ribozyme designed according to the guidelines of the invention is capable of accurate, effective trans-splicing in vitro.

Example 2

Design of a Trans-Splicing Ribozyme that Provides Plant Virus Resistance

Figure 5:
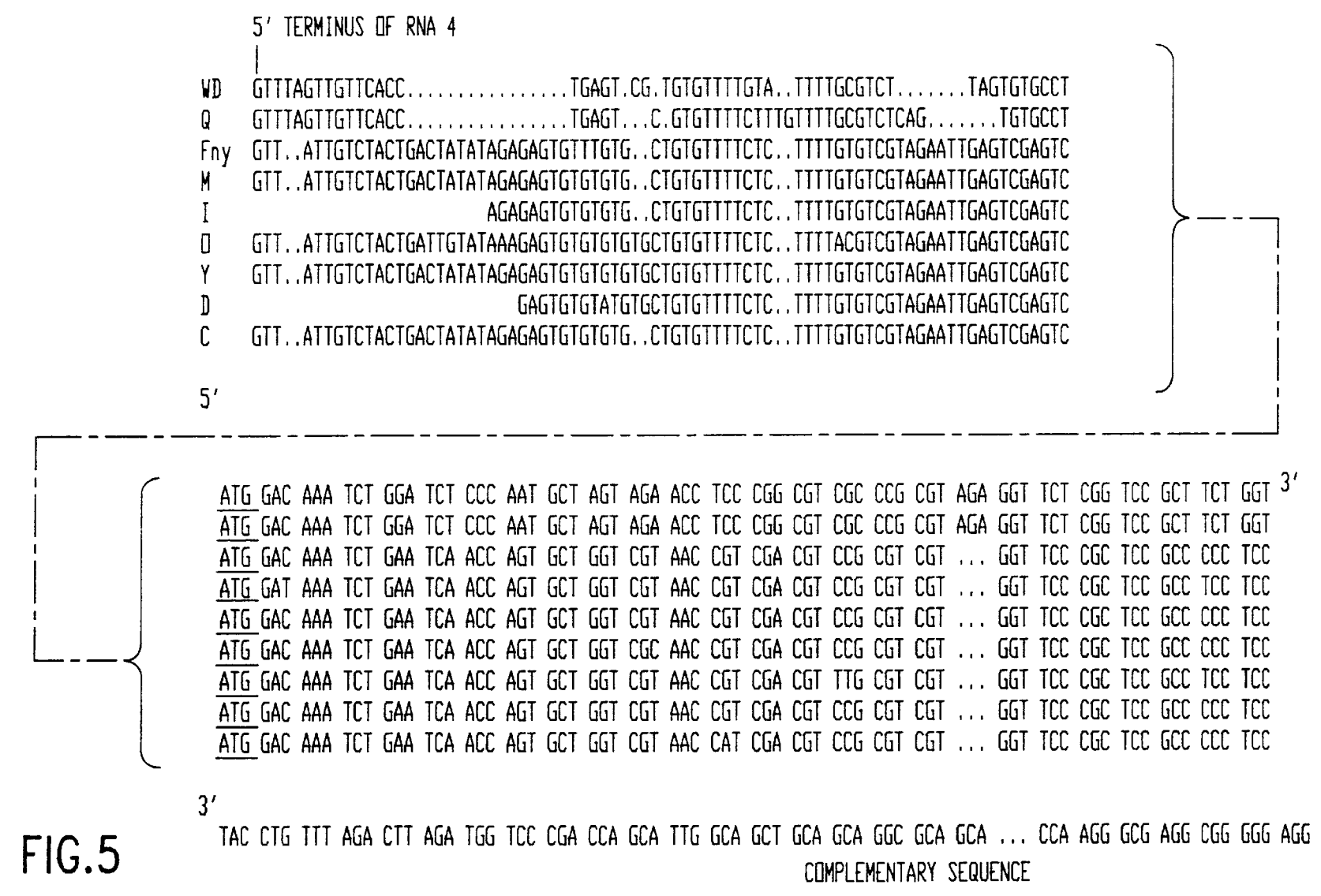

Cucumber mosaic virus (CMV) is a pandemic virus with a large number of known strains. Nine sequence strains are shown in the region of the start of their coat protein cistron encoded in RNA 3 and the subgenomic mRNA 4 (SEQ ID NOS. 7–25; FIGS. 4(A) and 5). Two sites have been chosen which are conserved in sequence and downstream from the AUG start codon of the coat protein. Oligonucleotides for the construction of ribozymes capable of trans-splicing the ile-mutant form of DTA into the CMV coat protein mRNA are shown in FIG. 4B and is discussed below.

The trans-splicing ribozymes shown in FIG. 4C are targetted to the CMV virus sequences shown in FIG. 4B and will result not only in the cleavage of the CMV RNA molecules but in the expression of diphtheria toxin A-chain in the infected cell. The trans-splicing cassettes shown in FIG. 4 may be transformed into any CMV-susceptible plant species using techniques known in the art, and transgenic progeny challenged by CMV infection. The design of the ribozyme is such that virus infection is necessary to initiate toxin production via RNA trans-splicing because the ribozyme itself is not translated. The localized death of the infected cells that results from expression of the toxin could limit replication and spread of the virus within the plant giving an artificial hypersensitive response.

Example 3

Construction and Characterization of a Gal4-Diphtheria Toxin A Chain Trans-Splicing Ribozyme According to the invention and the methods described in Example 1, a fusion ribozyme has been designed that is a Gal4-Diphtheria toxin A chain trans-splicing ribozyme (FIG. 6). The sequence of this ribozyme is shown as SEQ ID NO. 6. The GAL4-DTA ribozyme cassette is a SalI-XhoI fragment. The ScaI site marks a position 5 bases upstream of the 3' splice site. This ribozyme is capable of splicing the coding sequence for the A chain of the diphtheria toxin to a site in the 5' region of the GAL4 mRNA. This trans-splicing activity is active both in vitro (as above) and in vivo (below). The major criteria for successful design of the GAL4-DTA ribozyme, and any trans-splicing ribozyme that trans-splices a sequence encoding a toxic product, are not only the efficient and precise catalysis of trans-splicing, but also that expression of the toxic product, for example, DTA does not occur in the absence of trans-splicing.

The catalytic portion of the ribozyme is constructed according to the design outlined above, and 5' and 3' splice sites chosen within the 5' coding regions of GAL4 and DTA, respectively. The 3' exon sequence corresponds to that of a DTA gene already used for expression in eukaryotes, except for the removal of the first AUG codon and several proximal amino acids. The original *C. diphtheriae* form of DTA also differs in this 5' region, utilizing a CUG codon for translation initiation. The original DTA sequence also contains a signal peptide leader sequence which is absent.

These ribozyme molecules can undergo spontaneous scission at the 3' splice site. Given the extreme toxicity of DTA, it is important that any liberated 3' exon sequences not give rise to toxic translation products. The 3' exon contained an in-frame methionine at position 13, which could conceivably give rise to a truncated but toxic polypeptide. To eliminate this possibility, the wild-type sequence (Rz-$DTA_{met}$) was altered from methionine at this position to isoleucine (Rz-$DTA_{ile}$) or leucine (Rz-$DTA_{leu}$) in two separate ribozyme constructions (FIG. 6).

Example 4

In Vivo Activity of the Ribozymes of the Invention

I. Introduction

The in vivo activity of a ribozyme designed according to the guidelines provided herein, and the ability of such a ribozyme to deliver new gene activities to host cells, was demonstrated using the Gal4-Diphtheria toxin A chain trans-splicing ribozyme described (Example 3 and in FIG. 6) to deliver the highly toxic diphtheria toxin A product to a host cell. In this system, Drosophila was the chosen host and it was desired to control expression of the ribozyme of the invention in a tissue-specific manner within the Drosophila host.

Diphtheria toxin is secreted by *Corynebacterium diphtheriae* lysogenic for B phage. The toxin is produced as a single polypeptide which undergoes proteolysis to produce A and B chains. The A chain (DTA) contains a potent ADP ribosylase activity which is specific for the eukaryote translation elongation factor EF-2. The presence of even a few molecules of this enzyme is enough to cause cessation of translation and eventual death in a variety of eukaryote cells. The B chain allows intracellular delivery by attachment of the toxin to cell surface receptors by binding mannose residues, is endocytosed and enters the cytoplasm by vesicular fusion.

In the absence of the B-chain, the A-chain is much less toxic when present extracellularly. This property, and its extreme toxicity, have suggested its use for ectopic ablation experiments. For example, sequences encoding DTA have been expressed in transgenic mice, using an opsin promoter to drive expression in developing eyes. The resulting mice are blind, with deformed eyes (Breitman, M. L., *Science* 238:1563–1565 (1987)). In other studies, ablation of the mouse pancreas was performed (Palmiter, R. D. et al., *Cell* 50:435–443 (1987)) and Wert, S. E. et al., *Am. Rev. Respir. Dis.* 141 (no. 4, part 2):A695 (1990) described ablation of alveolar cells by use of a chimeric gene consisting of the promoter and 5' flanking sequence of the human surfactant protein C gene (expressed in type II alveolar cells) and the DTA gene.

However, using this type of approach, it is not possible to maintain or propagate transformed organisms which might have more severe, or lethal phenotypes. In addition, transformation of certain species, such as Drosophila, with intact DTA sequences has not been reported to date. Leaky expression of the DTA gene during such transformations leads to immediate death.

II. The Drosphila System

A general method for targeting gene expression in Drosophila has been developed. First, the system allows the rapid generation of individual strains in which ectopic gene expression can be directed to different tissues or cell types: the enhancer detector technique is utilized (O'Kane, C. J. and Gehring, W. J., *Proc. Natl. Acad. Sci. USA:*9123–9127 (1987); Bellen et al., *Genes and Development* 3:1288–1300 (1989); Bier et al., *Genes and Development* 3:1273–1287 (1989)) to express a transcriptional activator protein in a wide variety of patterns in embryos, in larvae and in adults. Second, the method separates the activator from its target gene in distinct lines, to ensure that the individual parent lines are viable: in one line the activator protein is present but has no target gene to activate, in the second line the target gene is silent. When the two lines are crossed, the target gene is turned on only in the progeny of the cross, allowing dominant phenotypes (including lethality) to be conveniently studied.

To ectopically express only the gene of interest, a transcriptional activator that has no endogenous targets in flies is required. An activator from yeast, Gal4, can activate transcription in flies but only from promoters that bear Gal4 binding sites (Fischer et al., *Nature* 332:853–865 (1988)). To target gene expression, Gal4 is restricted to particular cells in two ways: either Gal4 transcription is driven by characterized fly promoters, or an enhancerless Gal4 gene is randomly integrated in the Drosophila genome, bringing it under the control of a diverse array of genomic enhancers. To assay transactivation by Gal4, flies that express Gal4 are crossed to those bearing a lacZ gene whose transcription is driven by Gal4 binding sites (Fischer et al., *Nature* 332:853–865 (1988)). β-galactosidase is expressed only in those cells in which Gal4 is first expressed. Tissue- and cell-specific transactivation of lacZ has been demonstrated in strains in which Gal4 is expressed and in which a variety of patterns are established.

With this system, it is now possible: 1) to place Gal4 binding sites upstream of any coding sequence; 2) to activate that gene only within cells where Gal4 is expressed and 3) to observe the effect of this aberrant expression on development. In cases where ectopic expression is lethal, this method allows the two parent lines (one expressing Gal4, the other carrying a silent gene bearing Gal4 binding sites in its promoter) to be stably propagated. Phenotypes can then be studied in the progeny of a cross.

III. Vectors

The vectors utilized as starting materials in these studies include:

1) pGATB and pGATN (FIG. 9): These vectors are used for cloning promoters and enhancers upstream of a promoterless Gal4 gene.

Vectors were constructed in which either a unique NotI or BamHI site is inserted upstream of the Gal4 coding region. Once a promoter has been linked to the Gal4 coding sequence, the gene can be excised from the pHSREM vector backbone (Knipple and Marsella-Herrick, *Nucl. Acids Res.* 16:7748 (1988)) and moved into a P-element vector. The Rh2 promoter has been cloned (Mismer et al., *Genetics* 120:173–180 (1988)) into this vector and flies have been generated in which Gal4 is expressed only in the ocelli.

2) pGawB: This is a Gal4 vector for use in enhancer detection.

An enhancerless Gal4 gene was subcloned into the vector plwB (Wilson et al., *Genes and Development* 3:1301–1313 (1989)) to create pGawB. plwB was first digested with HindIII to remove the lacZ gene and the N-terminus of the P-transposase gene. These were replaced with the entire Gal4 coding region behind the TATA box of the P-transposase gene.

3) pUAST (FIG. 10): This plasmid was used for cloning coding sequences downstream of the Gal UAS.

A vector into which genes can be subcloned behind the Gal4 UAS (Upstream Activation Sequence) was constructed in the P-element vector, pCaSpeR3 (C. Thummel, Univ. of Utah Medical Center, Salt Lake City, Utah, personal communication). Five Gal4 binding sites were inserted, followed by the hsp70 TATA box and transcriptional start, a polylinker, and the SV40 intron and polyadenylation site. Unique sites into which genes, or cDNAs, can be inserted include: EcoRI, BglII, NotI, XhoI, KpnI and XbaI.

IV. Drosophila Strains

The genetic techniques described herein used to characterize the strains of Drosophila utilized in these studies are well known in the art ("Genetic Variations of *Drosophila melanogaster*," D. Lindsley and E. H. Grell, eds).

The P-element transposons are mobilized using the "jumpstarter" strain that carries Δ2–3, a defective P-element on the third chromosome that expresses high levels of a constitutively active transposase (Robertson et al., *Genetics* 118:451–470 (1988)). The three stocks currently used to generate and map the insertion lines were deposited in the Drosophila Stock Center, Indiana University Department of Biology, Jordan Hall A 503, Bloomington, Ind. 47405:

1: y w; +/+; Sb P[ry$^+$, Δ2–3]/TM6, Ubx

2: w; +/+; TM3, Sb/CxD (deposit no. 3665)

3: w; CyO/Sco; +/+(deposit no. 3666)

where the genetic characteristics of the three chromosomes are separated by semicolons. Thus, for example, in strain 1, the first chromosome (the X chromosome) is homozygous for yellow and white ("y w"), the second chromosome is wild-type ("+/+"), and the third chromosome carries the stubble gene ("Sb"), and the P element transposon rosy gene ("ry$^+$") and Δ2–3, while the second third chromosome carries balancer inversions ("/TM6, Ubx").

V. Strategy for Generating Gal4 Expression Patterns

A. Scheme used to isolate transformants

Constructs are injected into embryos derived from the stock;

♀♀ y w/y w ; Δ2-3,Sb/TM6,Ubx    X  ♂♂ y w/Y ; Δ2-3,Sb/TM6,Ubx
F0; Establish single lines
♀ y w/y w ; Δ2-3,Sb/TN6,Ubx    X  ♂ y w/Y; +/+
    or
♂ y w/Y ; Δ2-3,Sb/TN6,Ubx    X  ♀ y w/y w; +/+
F1; Select [w±] and [Sb±] progeny and establish stocks
♀ y w/y w ; +/TM6,Ubx    X  ♂ y w/Y; +/+
    or
♂ y w/Y ; +/TM6,Ubx    X  ♀ y w/y w; +/+

B. Schemes used to jump the enhancerless Gal4 insert

1. Jumps from the X-chromosome
♀♀ FM3/FM7,w; +/+                X ╲  ♂♂ y w/Y; Δ2-3,Sb/TM6,Ubx
♀♀ FM7,w/ P[Gal4,w$^+$]            ╱X  ♂♂ FM7/Y ; Δ2-3,Sb/+
♀♀ FM7,w/ P[Gal4,w$^+$];           ╱X  ♂♂ y w/Y; +/+
Δ2-3,Sb/+
♀ FM7,w/ y w ; Δ2-3,Sb/+       X  ♂ y w/Y; +/+
Select [w$^+$] and [B] progeny and establish stocks
2. Jumps from the Δ2-3-chromosome
♀♀ y w/y w                        X  ♂♂ y w/Y ;
                                       P[Gal4,w$^+$], Δ2-3,Sb/+
Select [w$^+$] and [Sb$^+$] progeny and establish stocks.

C. Chromosomal segregation

To analyze the segregation of the insertions two stocks are used: w;+/+; TM3, Sb/CxD and w; CyO/Sco;+/+.

Method

To create a large number of strains that express Gal4 in a cell- or tissue-specific manner enhancer detection vectors have been built that carry different versions of the Gal4 gene. Two genes, encoding either the full-length protein or a truncated protein, have been cloned into rosy (ry$^+$) and white (w$^+$) P-element vectors (modified versions of plArB and plwB; Wilson et al., *Genes and Development* 3:1301–1313 (1989)). Using ry$^+$ or w$^+$ as a screen, these vectors have been mobilized by introduction of the Δ2–3 gene (Robertson et al., *Genetics* 118:461–470 (1988)). To visualize the expression pattern of Gal4, the Gal4 insertion lines are crossed to a strain that carries the lacZ gene under the control of the Gal4 UAS (Fischer et al. *Nature* 332:853–865 1988). Embryos, larvae and adults derived from these crosses are screened for β-galactosidase expression either by an enzyme assay, with X-gal as a substrate, or by staining with monoclonal antibodies against β-galactosidase. β-galactosidase encoded by the UAS-lacZ construct is localized in the cytoplasm.

Approximately 500 Gal4-insertion strains have been screened and many that can be used to activate genes in specific tissues have been identified such as, for example, epidermal stripes, mesoderm, the central nervous system and the peripheral nervous system. Many of the lines express β-galactosidase in the salivary glands as well as in other tissues. It is possible that in constructing the enhancerless-Gal4 transposon a position-dependent salivary gland enhancer was fortuitously generated.

VI. Sample Screen

| # of Strains | No Staining | Salivary Gland | Other Tissues | % |
| --- | --- | --- | --- | --- |
| 9 | + | – | – | 5.8 |
| 45 | – | + | – | 28.8 |
| 61 | – | + | + | 51.9 |
| 21 | – | – | + | 13.5 |
| 156 | | | | 100.0 |

To activate a gene (Gene X) in a specific pattern, a Gal4 insertion line is selected and crossed to a strain that carries Gene X cloned behind the GAL UAS.

VII. Summary of the GAL4/UAS System without the Ribozyme

The Gal4/UAS system is a two-part system for controlling gene activation. The method is versatile, can be tissue-specific and does not appear to exhibit a basal level of expression except perhaps, as described herein, for a UAS-DTA construct. It can be used to ectopically express characterized genes, to express modified genes that would otherwise be lethal to the organism and to express genes from other species to study their effect on Drosophila development. Since the method makes it possible to produce dominant, gain-of-function mutations, epistasis tests and screens for enhancers or suppressors of visible or lethal phenotypes can be carried out. The Gal4 system also allows the expression of toxic products to study the consequences of cell- and tissue-specific ablation.

VIII. Use of Gal4-Expressing Drosophila with the DTA Ribozyme of the Invention

Figure 7:
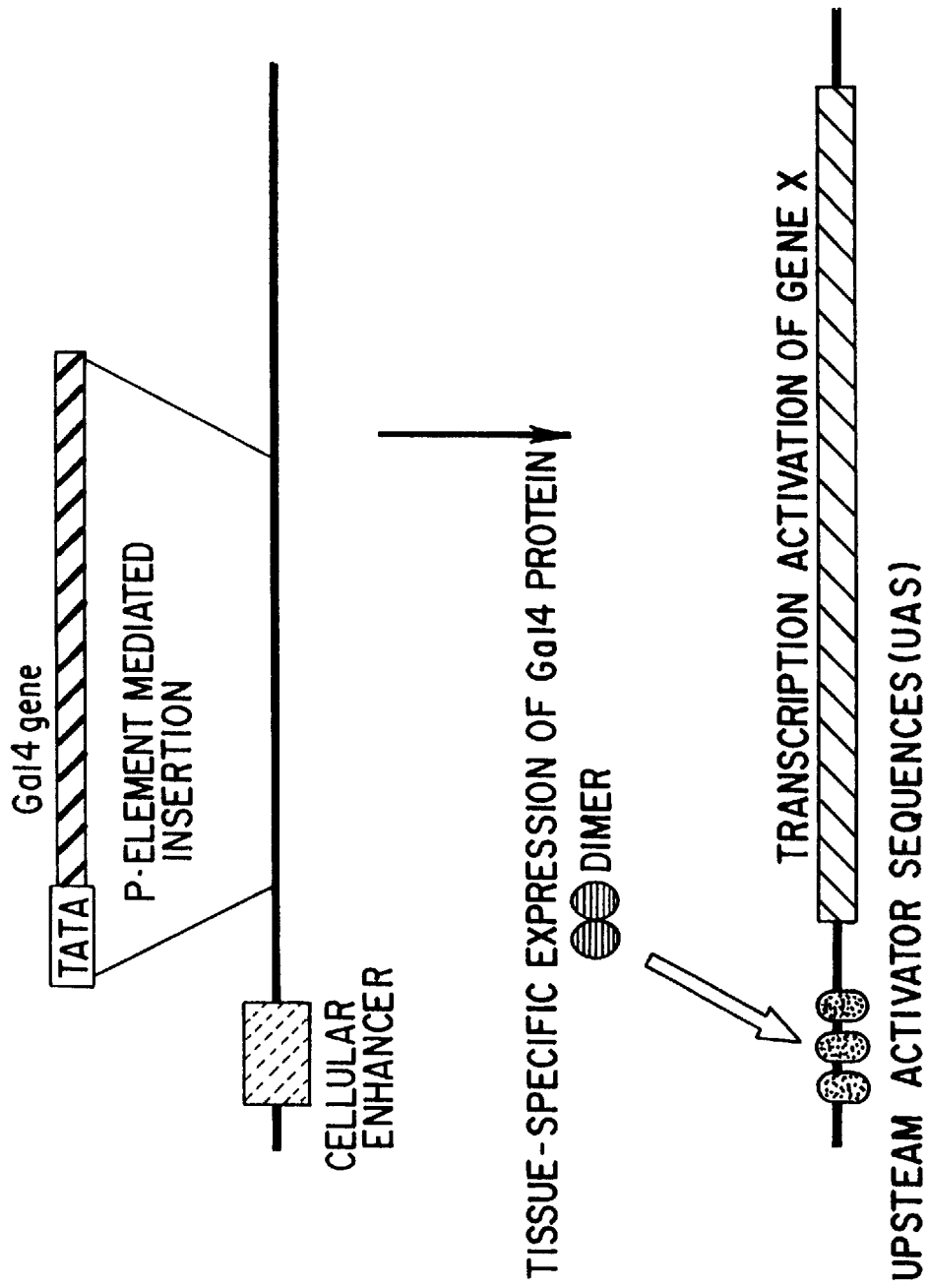
FIG. 7 is a diagram of the P-element mediated "enhancer-trapping" method for expression of Gal4 protein.
Figure 10:
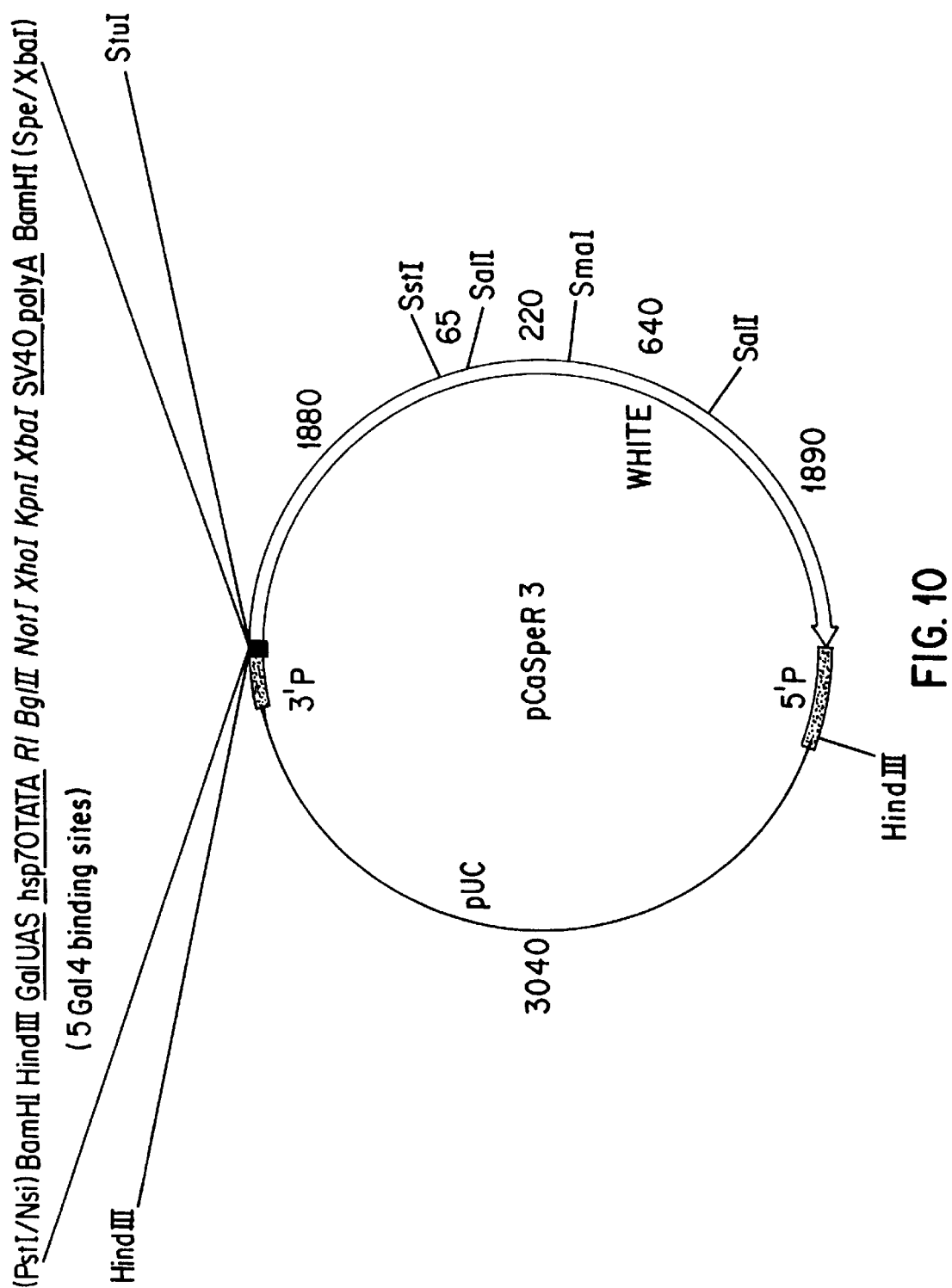
FIG. 10 is a map of Gal UAS vector (pUAST). Unique sites are indicated in italics.

Expression of the fusion ribozyme carrying the sequences encoding the DTA protein was placed under the control of a the GAL4 UAS (upstream activator sequence) in pUAST (FIG. 10). As stated supra, using modified P-element enhancer-trap vectors described above, a large number of stable lines of Drosophila were constructed which each express the yeast transcriptional activator GAL4 in specific spatial and temporal patterns in the developing flies. Any gene under the control of the GAL4 upstream activator sequence (UAS) can be transformed and maintained singly, then induced in particular Drosophila tissues by genetic crossing to lines which express GAL4 (FIG. 7). However, it was not possible to take advantage of the Gal4 system for expression of DTA per se without further modification, due to the difficulty in producing UAS-DTA transformants through leaky expression of the DTA.

It was found that use of this two-element system as a means of conditionally expressing DTA via a trans-splicing ribozyme (FIG. 6) overcame these problems. In those cells expressing GAL4, the GAL4 protein provides the activity necessary for ribozyme transcription, and the GAL4 mRNA provides the target for trans-splicing necessary for DTA production.

Drosophila embryos may be injected with ribozyme sequences placed under the control of a UAS promoter as described above, using techniques known in the art. Embryos injected with the Rz-DTA$_{met}$ construction will not survive, whereas normal transformed flies were obtained from embryos injected with both Rz-DTA$_{ile}$ and Rz-DTA$_{leu}$. This result suggested that the internal AUG codon was indeed acting as an initiation codon for the translation of a toxic product after injection. The codon is adjacent to a proposed NAD+ binding site in the DTA sequence, and to sequences conserved in the distantly related exotoxin A, another EF-2 specific ADP-ribosylase from *Pseudomonas aeruginosa*.

Figure 11:
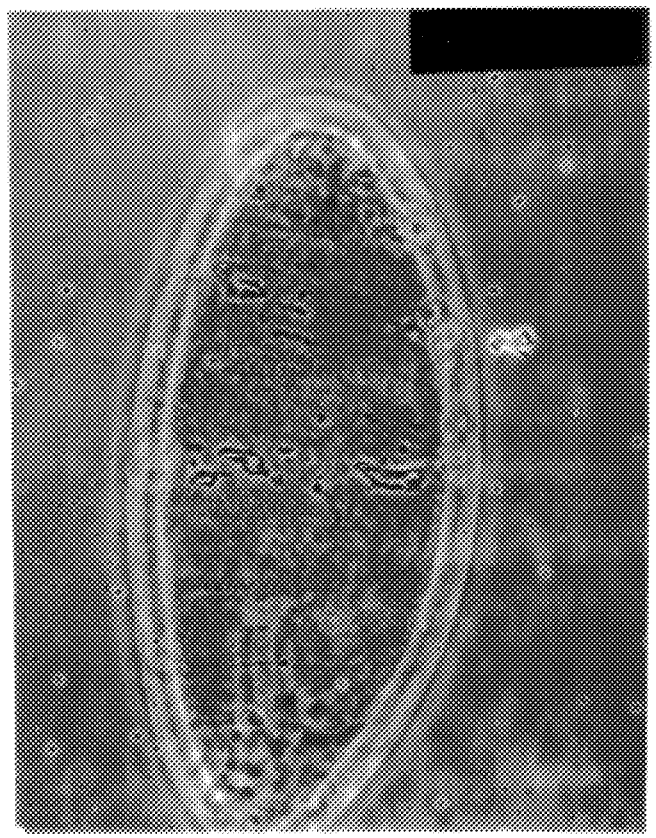
FIG. 11 is a cuticle preparation of a Drosophila embryos expressing a Gal4-DTA trans-splicing ribozyme.
Figure 12A:
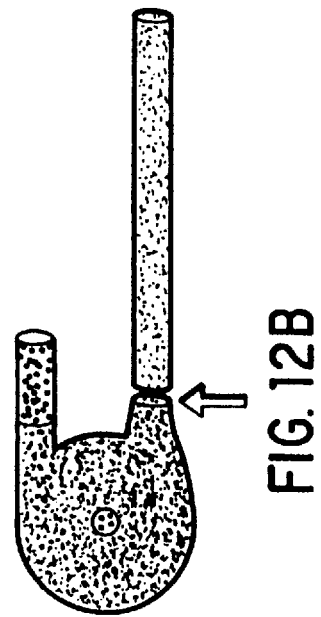
FIGS 12A–12D present the rationale for "pro-ribozyme" design. Arrows show sites of ribozyme cleavage, "antisense" regions are shown in black, catalytic domains are shown with radial shading, and 3' "exon" sequences are shown with light shading. In the absence of the target mRNA, trans-splicing ribozymes may transiently base-pair, and react with heterologous sequences (including their own). In addition, scission at the "3' exon" junction will occur. Inactive "pro-ribozymes" are constructed to contain extra self-complementary sequences which cause the catalytic center of the ribozyme to be mis-folded. Active ribozymes are only formed after base-pairing with the intended target mRNA—and consequent displacement of the interfering secondary structure.
Figure 12B:
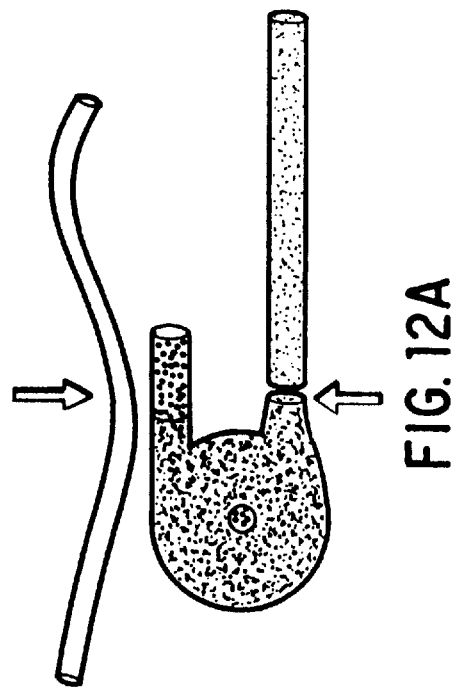
Figure 12C:
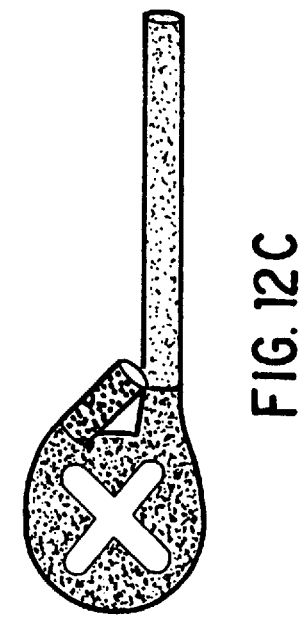
Figure 12D:
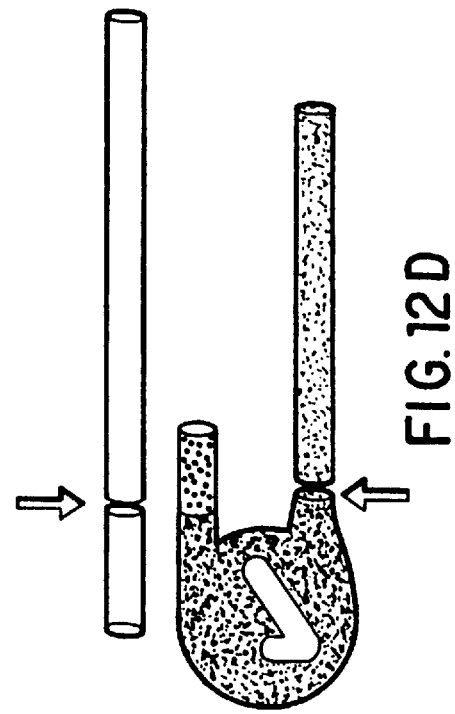

Transgenic flies containing the Rz-DTA$_{ile}$ and Rz-DTA$_{leu}$ sequences under control of the GAL4 UAS were crossed to flies producing GAL4 in particular patterns of expression. For example, in one characterized line, line 1J3, the GAL4 gene was been inserted near the hairy gene, and mirrored its pattern of expression. The hairy gene product is produced in epidermal stripes in the even-numbered abdominal segments during embryogenesis. When a UAS-driven LacZ gene was introduced into 1J3 in which GAL4 is expressed in the same pattern as the hairy gene product, β-galactosidase was found localized within the even-numbered stripes. When flies containing the Rz-DTA$_{leu}$ gene were crossed to this GAL4-expressing line, normal progeny resulted. However, when flies containing Rz-DTA$_{ile}$ were crossed to the GAL4-expressing line, development of the progeny was arrested in embryogenesis. Darker colored bands were evident on the cuticles of the embryos, consistent with the death of underlying cells. When cuticle preparations were examined, the even-numbered denticle bands were disrupted or missing, particularly those of the 4th, 6th and 8th stripes (FIG. 11). Other specific patterns of cell death were observed when the containing Rz-DTA$_{ile}$ flies are crossed to different GAL4 expressing genes.

Example 5

Design of Pro-ribozymes

Figure 8:
FIG. 8 presents a partial sequence of wild-type DTA and DTA 3' exon mutants and depicts prevention of toxin expression from splicing by-products.
Figure 9:
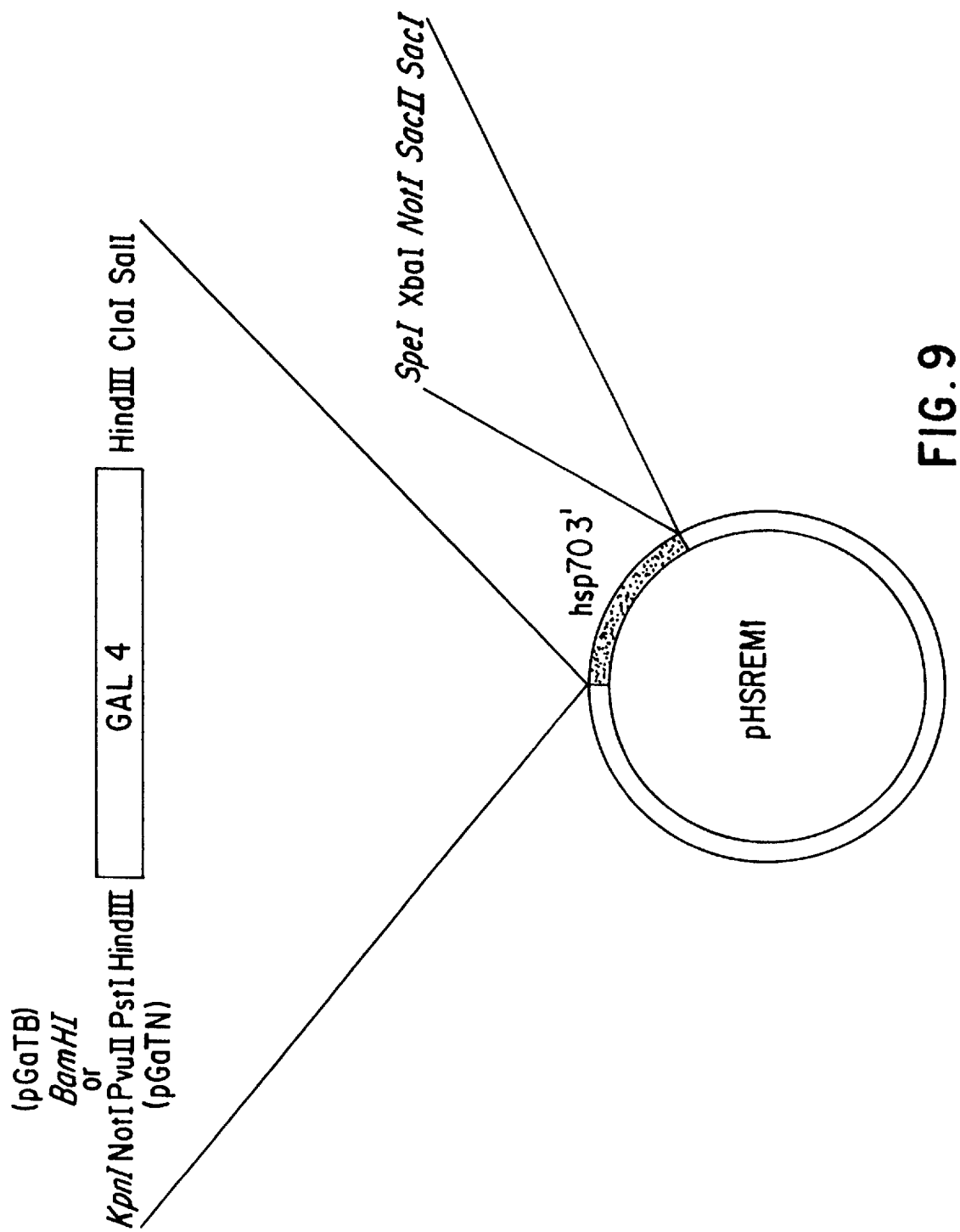
FIG. 9 is a map of Gal4 vector (pGaTB and pGaTN). Unique sites are indicated in italics; 3' NotI site is unique in pGatB only.
Figure 13:
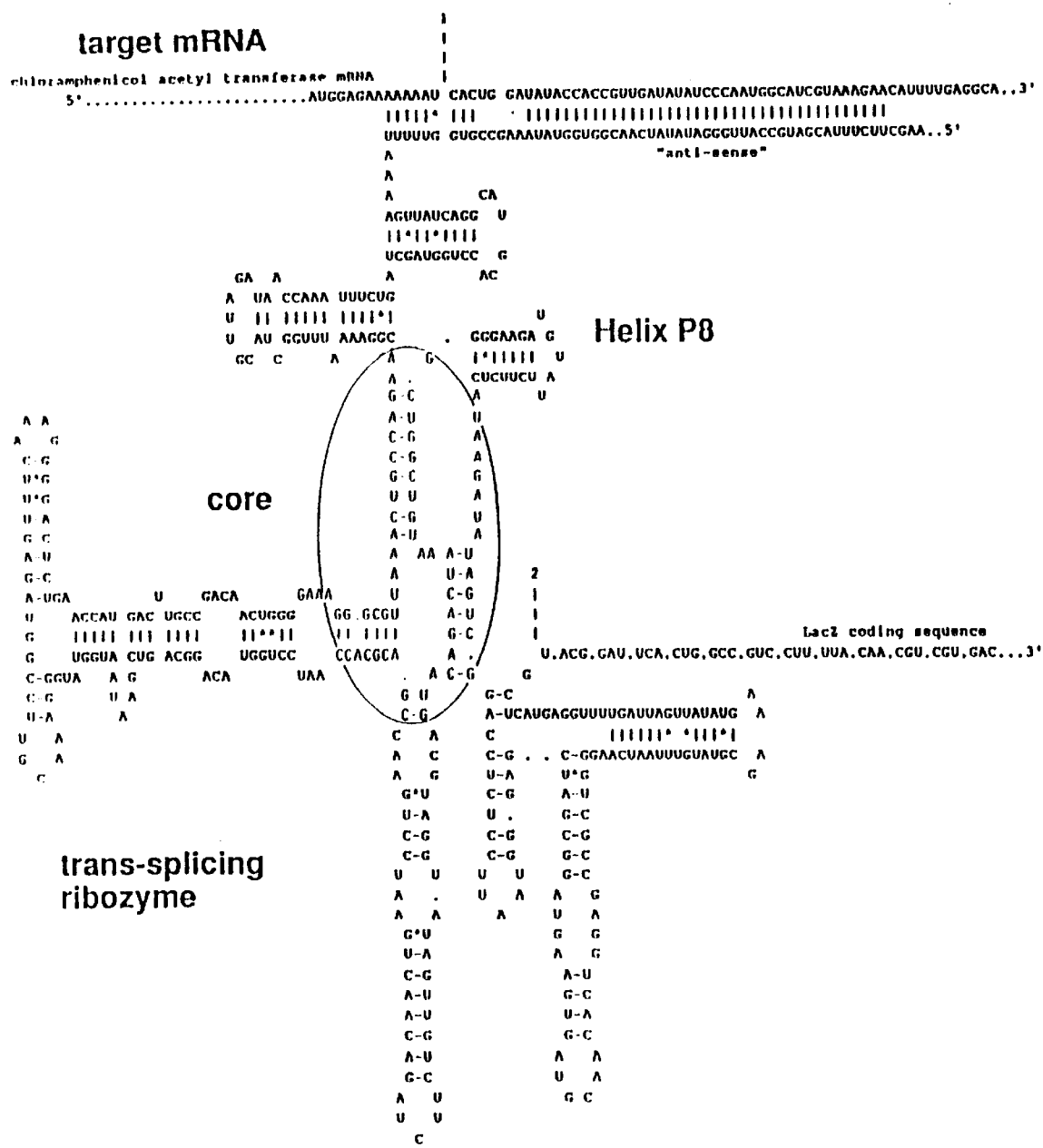
Figure 13A:
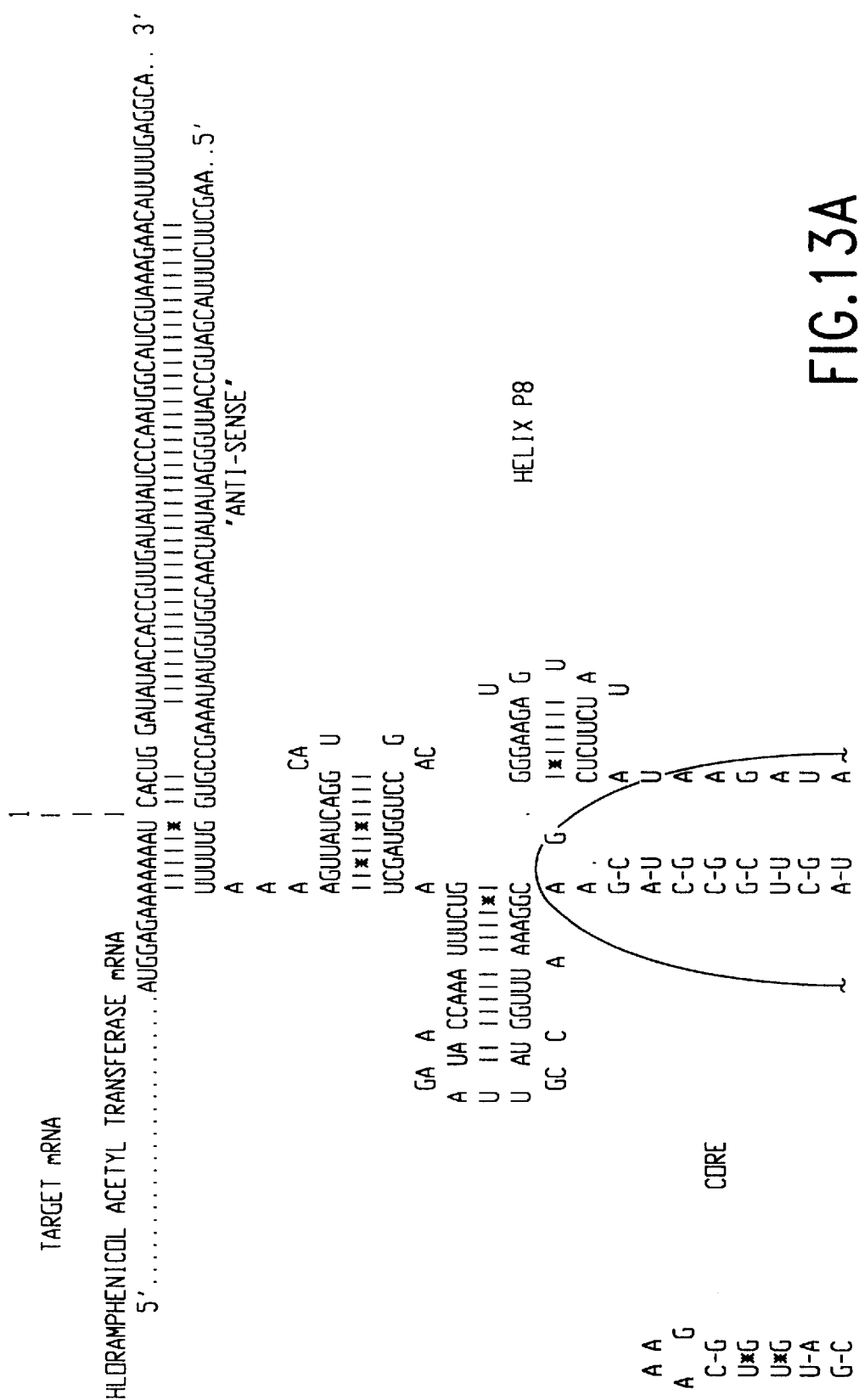
Figure 13B:
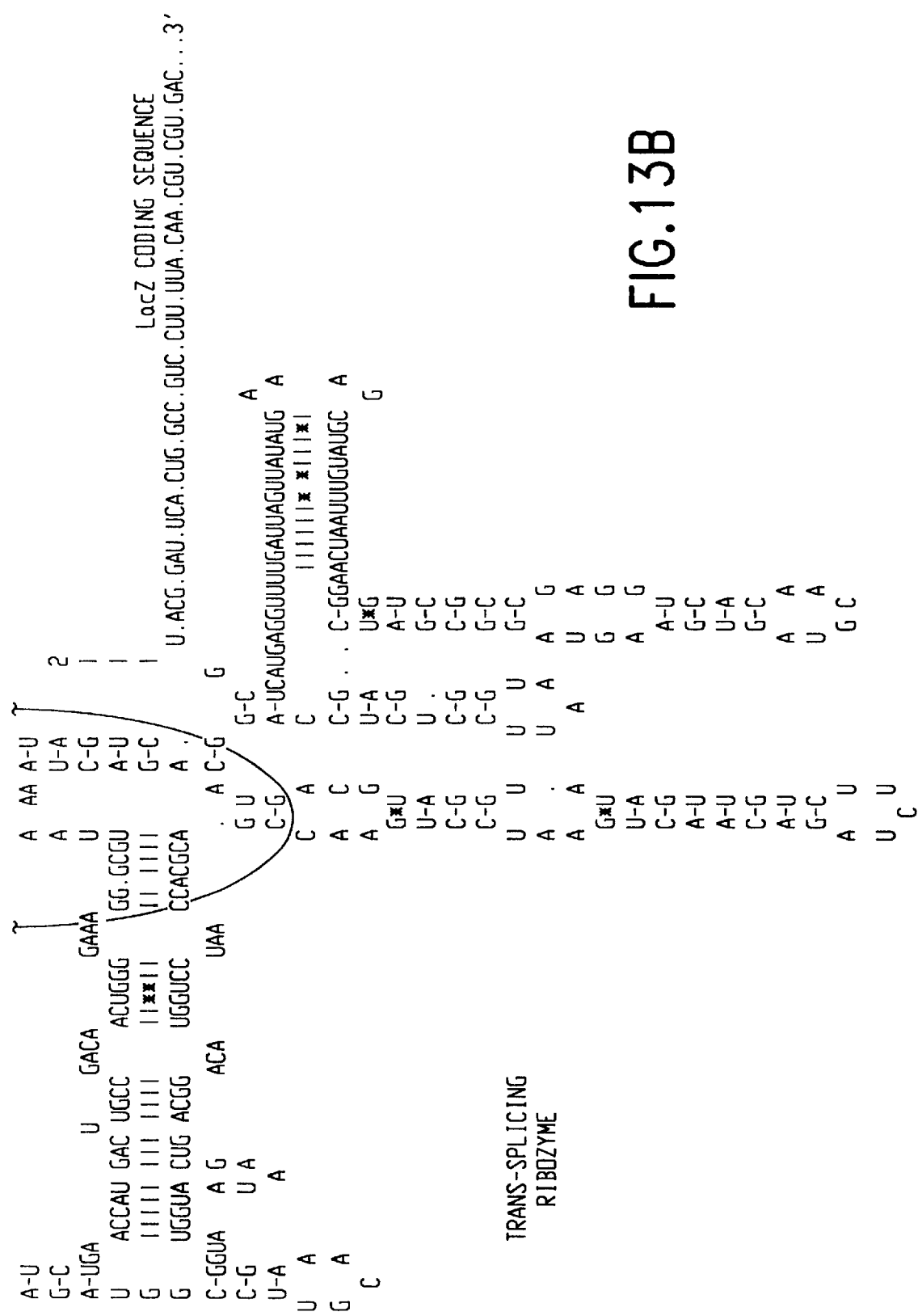
Figure 14A:
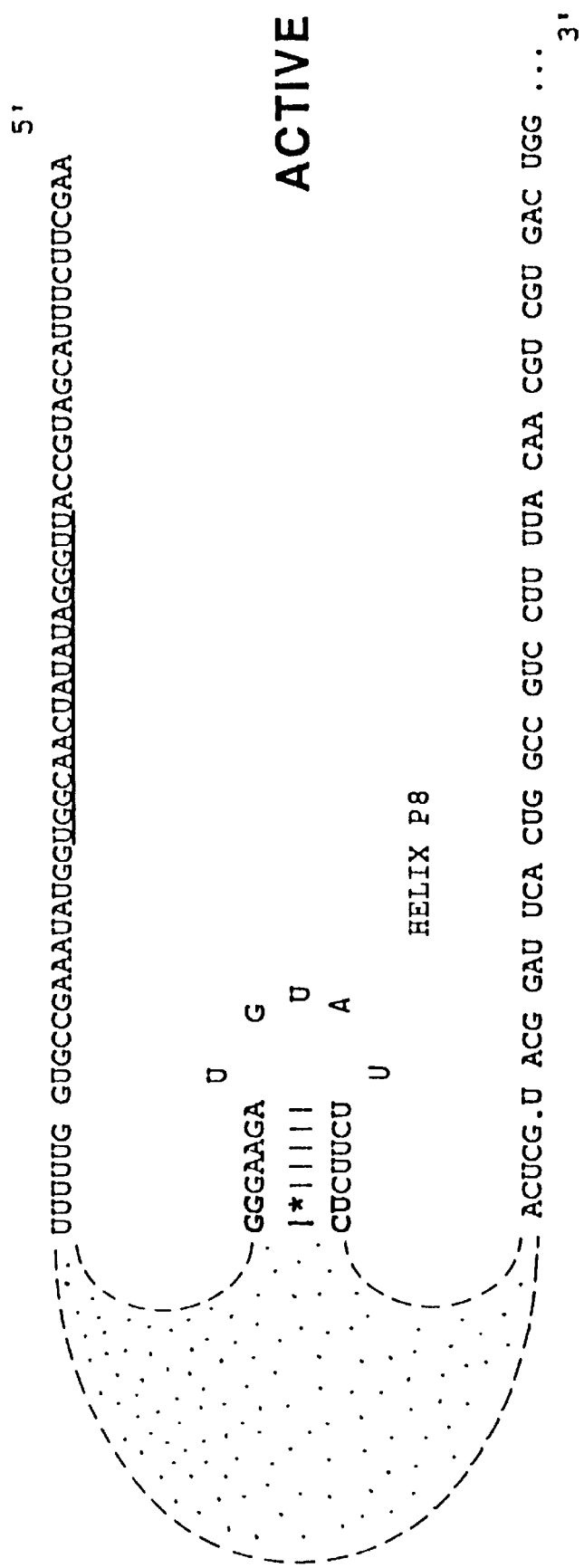
FIG. 14A shows active CAT-LacZ α-peptide trans-splicing ribozyme shown schematically, with "antisense", ribozyme domain with helix P8 and 3' "exon" sequences.
Figure 14B:
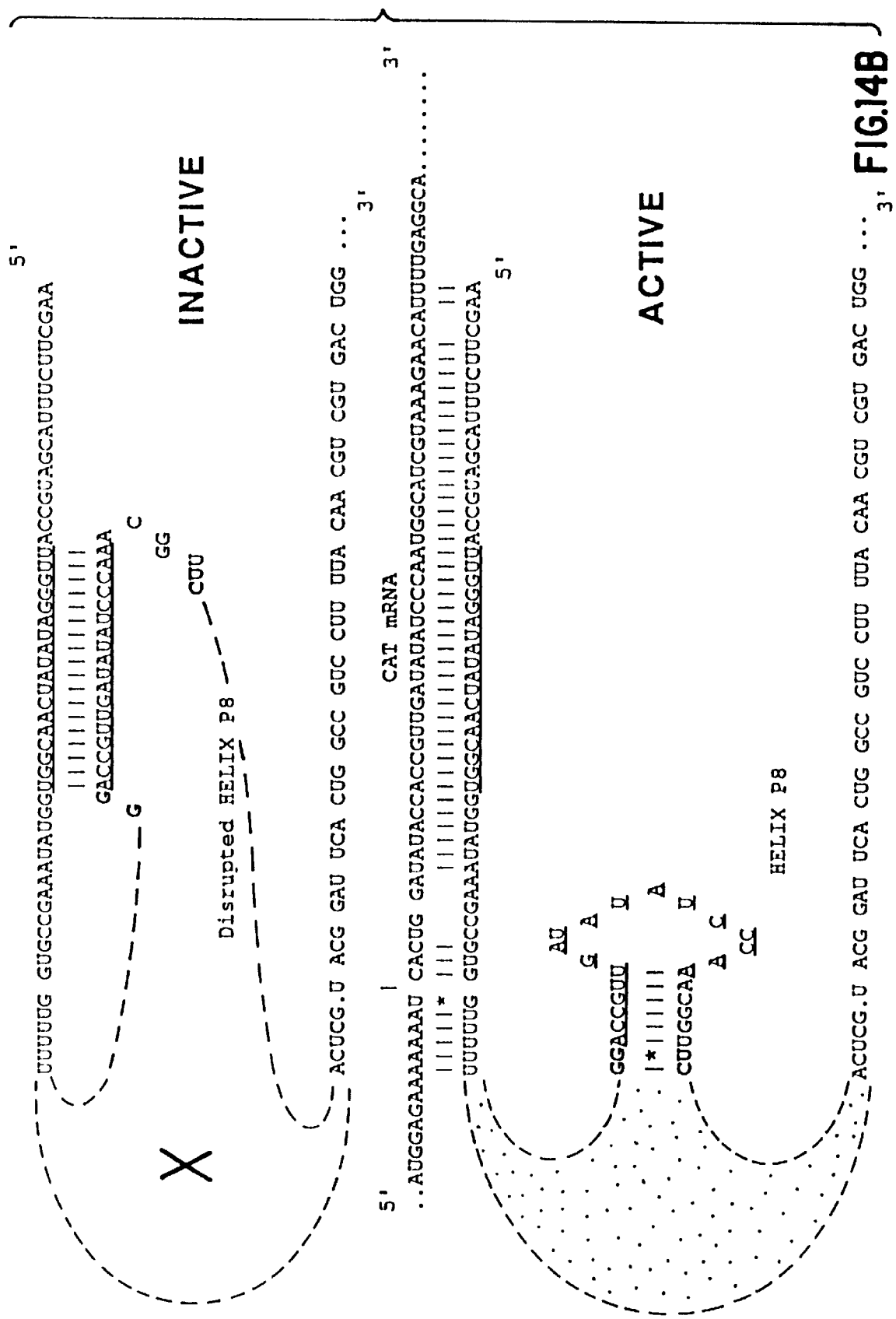
FIG. 14B, top, shows inactive CAT-LacZ α-peptide trans-splicing pro-ribozyme shown with base-pairing between sequences in the modified helix P8 and the "anti-sense" region.

As a test for the design of pro-ribozymes, the CAT-LacZ trans-splicing ribozyme which described earlier was modified (FIG. 2). Phylogenetic comparisons and mutational analysis (for review, see Cech, *Ann Rev. Biochem.* 59:543–568 (1990)) have indicated that a core region of the group I self-splicing introns is highly conserved and important for activity (FIG. 8). For the construction of trans-splicing pro-ribozymes a helix immediately adjacent to this region, P8, was disrupted. In the first experiments, 13 or 18 nucleotides of new sequence were introduced into the 5' strand and loop of helix P8, to produce pro-ribozyme 1 and 2, respectively. The extra nucleotides were complementary to the 5' "anti-sense" portion of the ribozyme, while the flanking sequences were adjusted to conserve (1) the actual sequences at the base of P8, and (2) the extent of base-pairing possible within P8 (FIG. 13). The extent of self-complementarity between the sequences inserted into helix P8 and the 5' "anti-sense" region of the pro-ribozyme is such that this new helix would be expected to form in nascent transcripts, in preference to helix P8. The formation of this alternative helix would also be expected to disrupt flanking secondary and perhaps tertiary interactions within the catalytic core of the ribozyme. Thus, mis-folding of the pro-ribozyme would render it catalytically inactive (FIG. 14). However, base-pairing of the pro-ribozyme with the intended target RNA would displace the P8-"anti-sense" base-pairing, sequester the "anti-sense" sequences and allow re-formation of the P8 helix and an active catalytic domain. Displacement of the P8-"anti-sense" helix results in a greater sum of base-pairs and allows proper folding of the catalytic domain, so should be energetically favored.

CAT-LacZ pro-ribozymes

Figure 15:
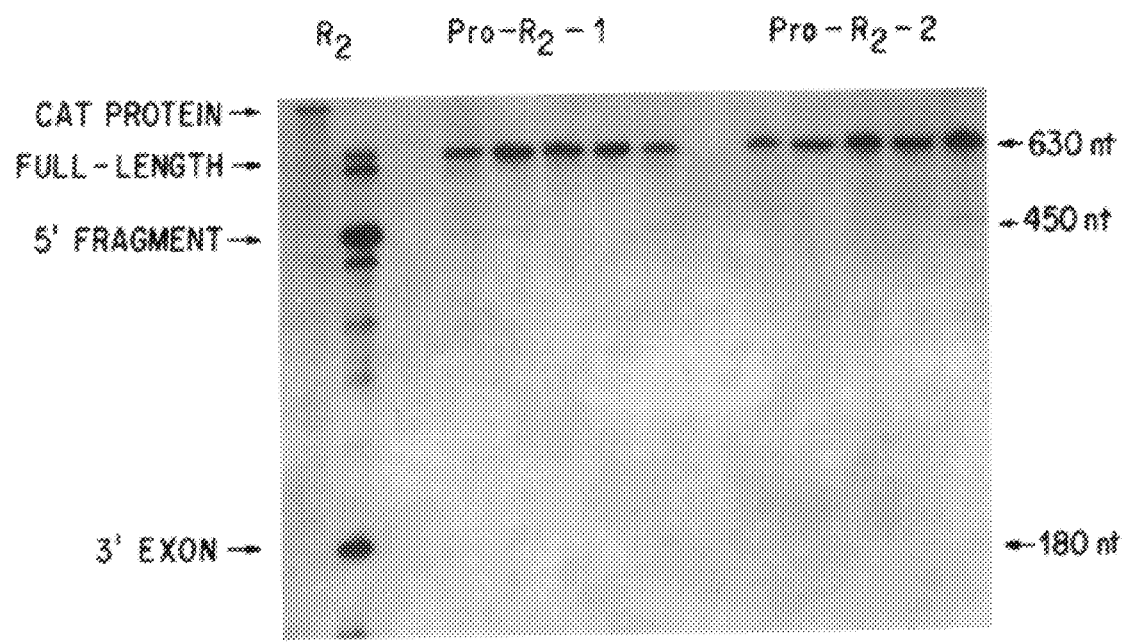
FIG. 15 shows stability of CAT-LacZ pro-ribozyme transcripts. Plasmids containing the CAT-LacZ ribozyme and pro-ribozyme sequences were cleaved with EcoRI and transcribed using T7 or SP6 RNA polymerase and [32-P]UTP. Radiolabeled transcripts were fractionated by 5% polyacrylamide gel electrophoresis in 7M urea and 25% formamide, and autoradiographed. The ribozyme transcripts underwent extensive hydrolysis, primarily at the "3' exon" junction. The pro-ribozyme forms were markedly less reactive.
Figure 16:
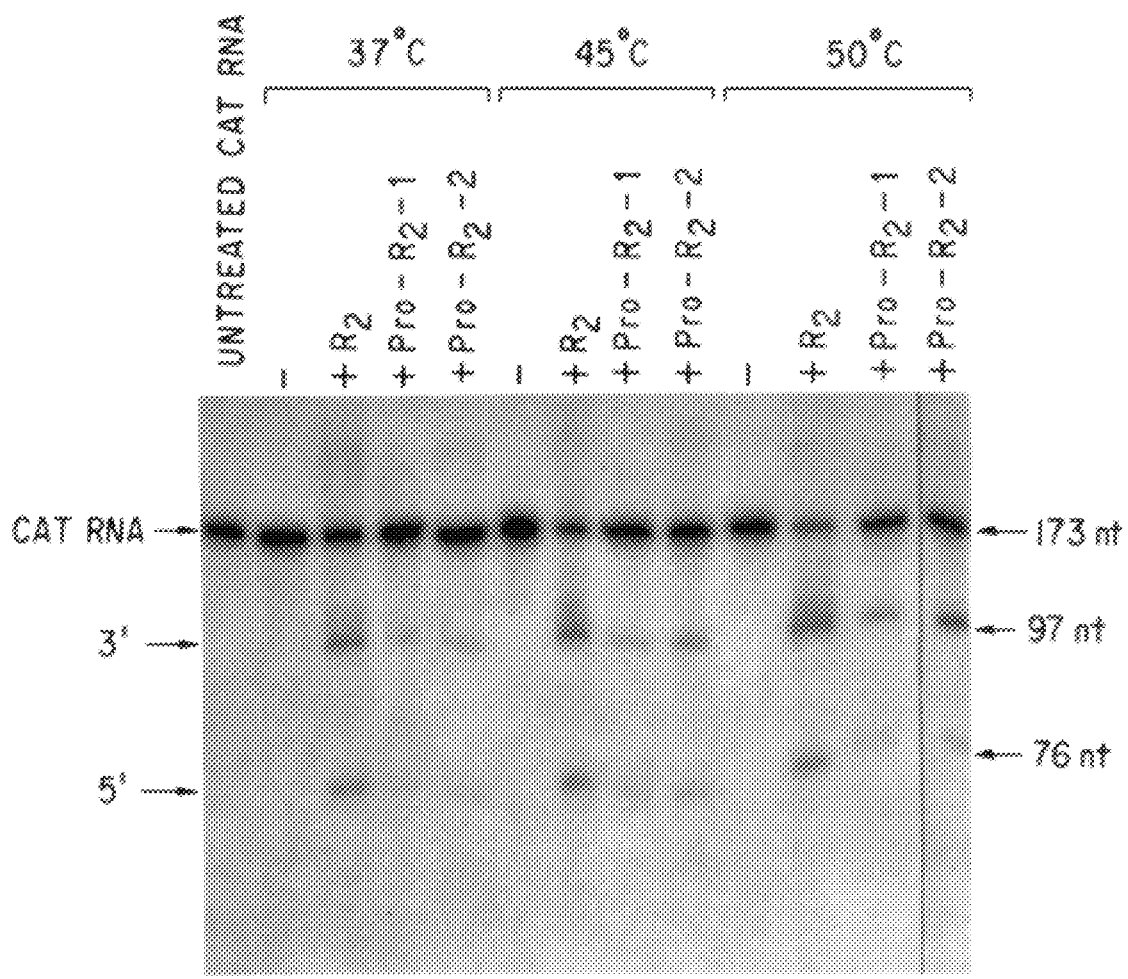
FIG. 16 shows endoribonuclease activity of CAT-LacZ pro-ribozymes. Plasmids containing CAT-LacZ ribozyme and pro-ribozyme sequences were cleaved, with ScaI, and transcribed with T7 or SP6 RNA polymerase. Transcripts were incubated for 30' at 37° C., 45° C. and 50° C. in 40 mM Tris-HCl pH 7.5, 6 mM MgCl$_2$, 2 mM spermidine, 10 mM NaCl, 2 mM GTP with radiolabeled CAT RNA, transcribed using T7 RNA polymerase from plasmid cut with PuvII. Products were fractionated by 5% polyacrylamide gel electrophoresis in 7M urea and 25% formamide, and autoradiographed. RNA mediated cleavage of the 173 nt (nucleotides) CAT RNA produces 5' and 3' fragments of 76 nt and 97 nt, respectively.

Cloned sequences corresponding to the two CAT-LacZ pro-ribozymes were constructed using PCR-mutagenesis as discussed above, and RNAs were produced by in vitro transcription. The CAT-LacZ trans-splicing ribozyme was observed to undergo scission during transcription at the 3' splice junction, as a result of hydrolysis catalyzed by the intron sequences. Similar hydrolysis is seen in in vitro transcripts of the unmodified *Tetrahymena thermophila* intron. In contrast, transcripts of the different CAT-LacZ pro-ribozymes are more stable, with little cleavage evident under the same conditions (FIG. 15). This indicates that the pro-ribozymes are inactive, which would be expected if the catalytic sequences were mis-folded. Truncated forms of the pro-ribozymes were tested for specific endoribonuclease activity directed against the CAT RNA. CAT-LacZ pro-ribozyme RNAs were transcribed from templates truncated at the ScaI site, to remove the 3' splice junction and LacZ sequences. Both ribozyme and pro-ribozyme RNAs are stable after removal of the 3' splice site. Incubation of the truncated pro-ribozymes with CAT RNA led to specific cleavage of the target RNA to give fragments of the expected sizes (FIG. 16). Specific cleavage activity was seen at 37, 45 and 50 degrees.

Figure 18:
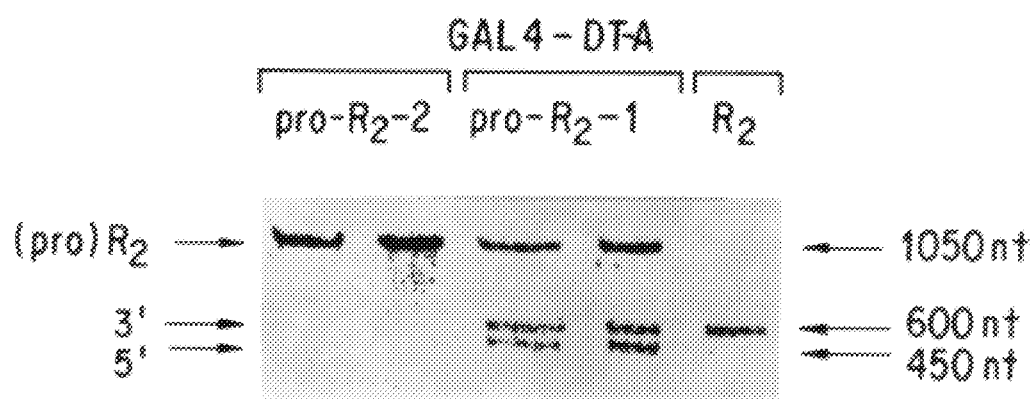
FIG. 18 shows the stability of GAL4-DTA pro-ribozymes. Plasmids containing ribozyme and pro-ribozyme sequences were linearized with XhoI and transcribed using T7 RNA polymerase. Transcripts were incubated for 60' at 50° C. in 40 mM Tris-HCl pH 7.5, 6 mM MgCl$_2$, 2 mM spermidine, 10 mM NaCl, 1 mM GTP, were fractionated by 5% polyacrylamide gel electrophoresis in 7M urea and 25% formamide, and autoradiographed. Ribozyme transcripts are extensively hydrolysed under these conditions, while pro-ribozyme 1 is less so and pro-ribozyme 2 is stable.

Pro-ribozyme forms of the GAL4-DTA trans-splicing ribozyme were also constructed (FIG. 17). Regions of 20 nucleotides (complementary to the "anti-sense" region) were inserted into the 5' strand and loop of helix P8. The two pro-ribozymes differed in the extent of base-pairing possible in the modified helices P8, and GAL4-DTA pro-ribozyme 1 possessing both a longer stem and fewer (3) accessible bases in the loop. The helix P8 of GAL4-DTA pro-ribozyme 2 more closely resembles that of the CAT-LacZ pro-ribozyme 2, with a larger loop (14 bases) containing sequences complementary to the "anti-sense" region. Transcripts of the GAL4-DTA pro-ribozymes are more stable than those of the unmodified ribozyme. In particular, pro-ribozyme 2 is mainly intact after incubation in conditions that result in essentially complete self-cleavage of the ribozyme form (30' @ 50° C., 10 mM MgCl$_2$, 2 mM GTP, see FIG. 18).

Having now fully described the invention, it will be understood by those with skill in the art that the scope may be performed within a wide and equivalent range of conditions, parameters and the like, without affecting the spirit or scope of the invention or any embodiment thereof.

What is claimed is:

1. A method for cell ablation in multicellular animals, said method comprising introducing into the genome of a fertilized embryonic host cell, a polynucleotide molecule, said polynucleotide molecule encoding a trans-splicing Group I ribozyme, the sequence of said ribozyme being a fusion RNA, the sequence of such fusion RNA comprising:

(1) a first RNA sequence, which hybridizes to a target RNA that encodes a transcription activator protein, and (2) a second RNA sequence, which is to be trans-spliced into said target RNA; wherein said polynuceotide molecule is operably linked to a transcription regulatory element which is specifically recognized by said transcription activator protein such that association of said transcription activator protein with said transcription regulatory element results in activation of transcription of said polynucleotide molecule and production of said trans-splicing ribozyme only in a cell which is to be ablated; said ribozyme encoding the sequence of a peptide toxic to the cell which is to be ablated and said ribozyme trans-splicing said sequence into a target in said cell; wherein the target RNA encoding the transcription activator protein is produced under control of a tissue-specific promoter that operates specifically in the tissue to be ablated.

2. The method of claim 1, wherein an RNA sequence that hybridizes to said first RNA sequence is inserted into the P8 helix of a pro-ribozyme.

3. The method of claim 1, wherein said transcription activator protein is GAL4; and wherein said first RNA sequence is a sequence that hybridizes to GAL4 RNA.

4. The method of claim 1, wherein said toxic peptide is the DTA peptide.

5. The method of claim 1, wherein said DTA peptide is a mutant peptide sequence.

6. The method of claim 1, wherein said mutant peptide sequence comprises amino acids encoded by SEQ ID. No. 40.

7. The method of claim 1, wherein said mutant peptide sequence comprises amino acids encoded by SEQ ID. No. 41.

8. The method of claim 3, wherein said second RNA sequence is a sequence that encodes the DTA peptide.

9. The method of claim 8, wherein said DTA peptide is a mutant peptide sequence.

10. The method of claim 8, wherein said mutant peptide sequence comprises amino acids encoded by SEQ ID. No. 40.

11. The method of claim 8, wherein said mutant peptide sequence comprises amino acids encoded by SEQ ID. No. 41.

* * * * *